US012186521B2

(12) United States Patent
Jiang

(10) Patent No.: US 12,186,521 B2
(45) Date of Patent: Jan. 7, 2025

(54) UNIVERSAL DISINFECTING CAP

(71) Applicant: Becton, Dickinson and Company, Franklin Lakes, NJ (US)

(72) Inventor: Chang Jiang, Butler, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 882 days.

(21) Appl. No.: 17/271,124

(22) PCT Filed: Sep. 12, 2019

(86) PCT No.: PCT/US2019/050790
§ 371 (c)(1),
(2) Date: Feb. 24, 2021

(87) PCT Pub. No.: WO2020/056120
PCT Pub. Date: Mar. 19, 2020

(65) Prior Publication Data
US 2021/0244933 A1    Aug. 12, 2021

Related U.S. Application Data

(60) Provisional application No. 62/731,188, filed on Sep. 14, 2018.

(51) Int. Cl.
*A61M 39/16* (2006.01)
*A61M 39/20* (2006.01)
*A61M 39/10* (2006.01)

(52) U.S. Cl.
CPC .......... *A61M 39/162* (2013.01); *A61M 39/20* (2013.01); *A61M 2039/1033* (2013.01);
(Continued)

(58) Field of Classification Search
CPC ................. A61M 39/162; A61M 39/20; A61M 2205/0205; A61M 39/16
See application file for complete search history.

(56) References Cited

U.S. PATENT DOCUMENTS 5,407,437 A * 4/1995 Heimreid ............... A61M 39/02
604/83
5,554,135 A * 9/1996 Menyhay ............... A61M 39/20
604/539
(Continued)

FOREIGN PATENT DOCUMENTS

JP    2001309973 A    11/2001
JP    2016506856 A    3/2016
(Continued)

OTHER PUBLICATIONS

PCT International Search Report and Written Opinion in PCT/US2019/050790 dated Nov. 26, 2019, 10 pages.

*Primary Examiner* — Nathan R Price
*Assistant Examiner* — Haden Matthew Ritchie
(74) *Attorney, Agent, or Firm* — Servilla Whitney LLC

(57) ABSTRACT

A device for connection to a medical connector, the device includes a cap body, a coupling cylinder adapted to engage with a male luer connector and a female luer connector, a bulb compartment filled with air, a reagent compartment filled with disinfectant or an antimicrobial reagent, and a passageway connecting the bulb compartment to the reagent compartment. The reagent compartment includes an exterior wall surface, an interior wall surface, an array of resealable pores densely integrated throughout the exterior wall surface and the interior wall surface of the reagent compartment, and a distal tip. The passageway may be positioned in an aperture of the proximal wall of the cap body. The coupling cylinder may include an O-ring.

17 Claims, 20 Drawing Sheets

(52) U.S. Cl.
CPC ............... *A61M 2039/1083* (2013.01); *A61M 2039/1088* (2013.01); *A61M 2205/0205* (2013.01); *A61M 2205/0216* (2013.01)

(56) References Cited

U.S. PATENT DOCUMENTS

| | | |
|---|---|---|
| 9,809,355 B2 | 11/2017 | Solomon et al. |
| 2003/0072696 A1* | 4/2003 | Higa .................... F02M 27/045 422/186.01 |
| 2009/0008393 A1 | 1/2009 | Howlett et al. |
| 2013/0197485 A1* | 8/2013 | Gardner .............. A61M 39/162 604/533 |
| 2016/0045629 A1 | 2/2016 | Gardner et al. |
| 2016/0106969 A1* | 4/2016 | Neftel ................. A61M 39/165 29/426.1 |
| 2016/0158520 A1* | 6/2016 | Ma .................... A61M 25/0017 604/265 |
| 2018/0256880 A1 | 9/2018 | Follman et al. |

FOREIGN PATENT DOCUMENTS

| | | |
|---|---|---|
| KR | 100957258 B1 | 5/2010 |
| WO | 2006019782 A2 | 2/2006 |
| WO | 2014159346 A1 | 10/2014 |
| WO | 2016085815 A1 | 6/2016 |
| WO | 2018106508 A1 | 6/2018 |

* cited by examiner

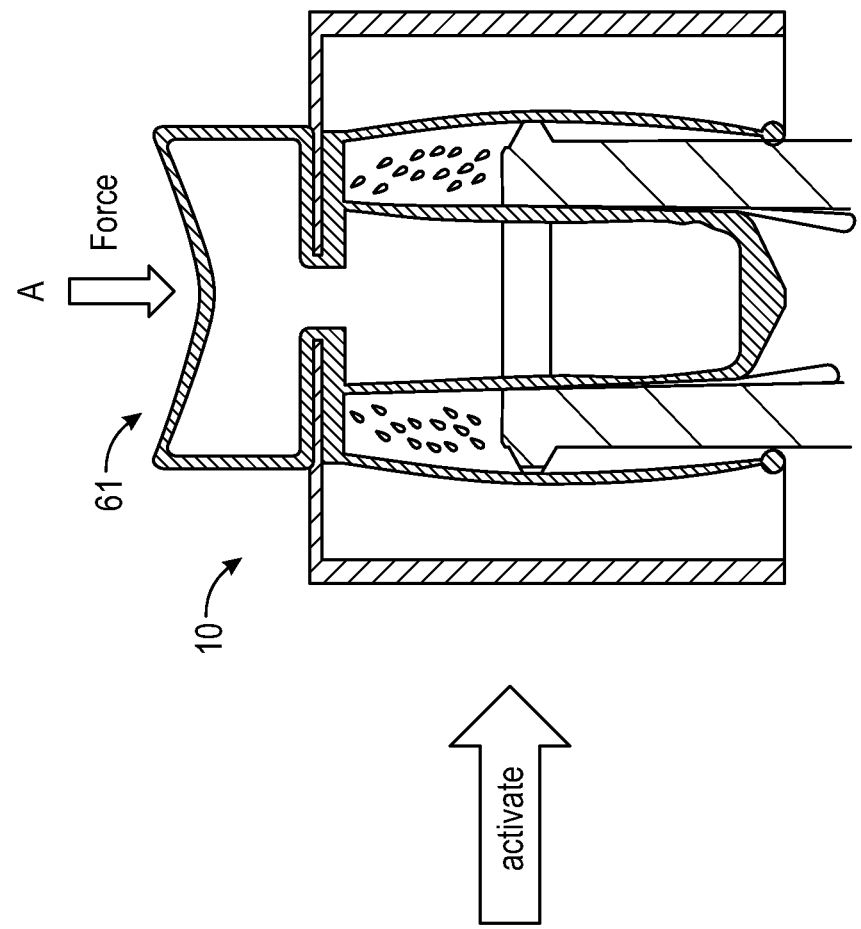
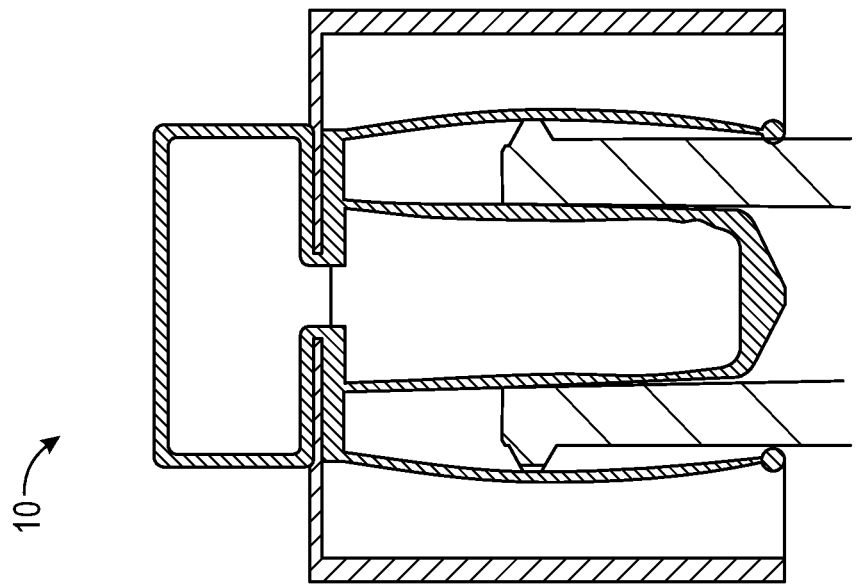
FIG. 11

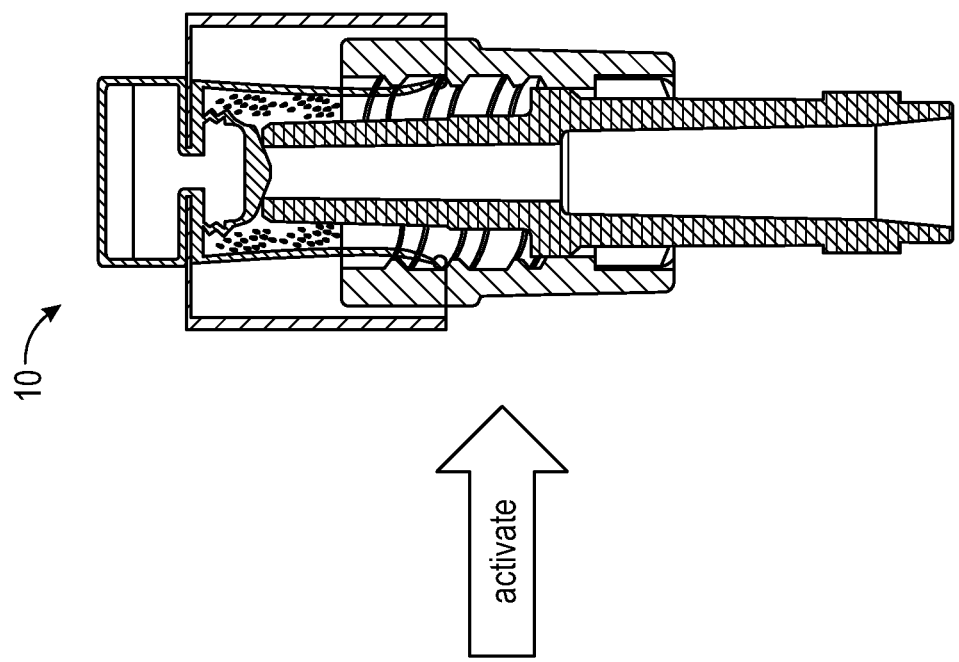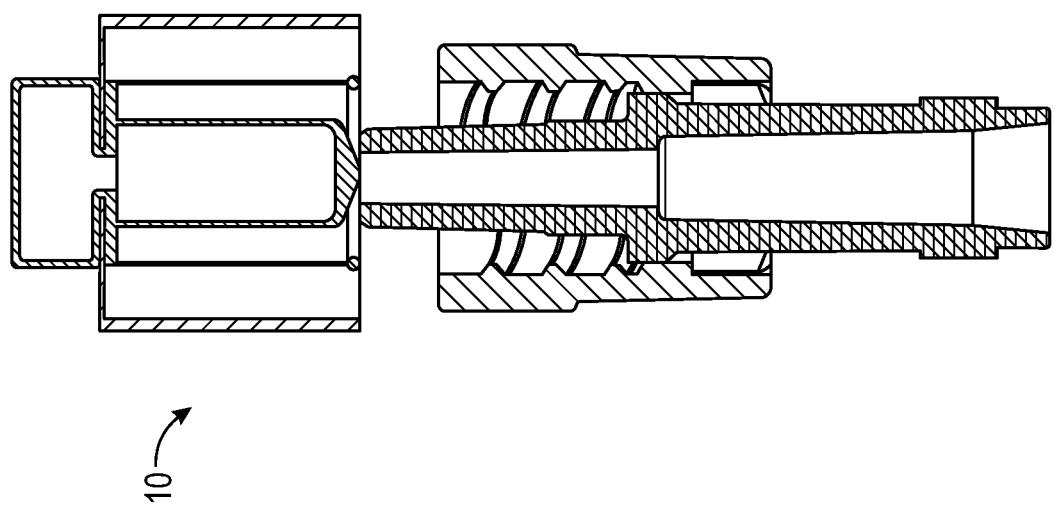
FIG. 12

UNIVERSAL DISINFECTING CAP

CROSS-REFERENCE TO RELATED APPLICATIONS

This application is the National Stage entry of PCT/US19/50790, filed on Sep. 12, 2019, which claims priority to U.S. Provisional Patent Application No. 62/731,188, filed Sep. 14, 2018, the entire disclosures of which are hereby incorporated by reference herein.

TECHNICAL FIELD

The present disclosure generally relates to a device for disinfecting and sterilizing access ports with, e.g., male and female luer fitting, and, in particular, to disinfecting and sterilizing devices capable of accommodating multiple types of connectors.

BACKGROUND

Vascular access devices (VAD's) are commonly used therapeutic devices and include intravenous (IV) catheters. There are two general classifications of VAD's, peripheral catheters and central venous catheters. Bacteria and other microorganisms may gain entry into a patient's vascular system from access hubs, ports or valves upon connection to the VAD to deliver the fluid or pharmaceutical. Each access hub, port, valve or connection is associated with some risk of transmitting a catheter related bloodstream infection (CRBSI), which can be costly and potentially lethal.

In order to decrease catheter-related bloodstream infection (CRBSI) cases and to ensure VAD's are used and maintained correctly, standards of practice have been developed, which include disinfecting and cleaning procedures. Disinfection caps have been added to the Society for Healthcare Epidemiology of America (SHEA) guidelines and early indications are that caps will also be incorporated into the Infusion Nurses Standards (INS) guidelines.

In developed markets, when utilizing an IV catheter, a needleless connector will typically be used to close off the system and then subsequently accessed to administer medication or other necessary fluids via the catheter to the patient. INS Standards of Practice recommend the use of a needleless connector and state that it should be "consistently and thoroughly disinfected using alcohol, tincture of iodine or chlorhexidine gluconate/alcohol combination prior to each access." The disinfection of the needleless connector is ultimately intended to aid in the reduction of bacteria that could be living on the surface and possibly lead to a variety of catheter related complications including the CRBSI events described earlier. Nurses will typically utilize a 70% IPA alcohol pad to complete this disinfection task by doing what is known as "scrubbing the hub." However, compliance to this practice is typically very low. In addition to a lack of compliance to "scrubbing the hub", it has also been noted through clinician interviews that there is often a variation in scrub time, dry time and the number of times the needleless connector is scrubbed.

Throughout the sequence of procedures associated with the transmission of a microorganism that can cause a CRBSI, there are many risks of contact or contamination. Contamination can occur during drug mixing, attachment of a cannula, and insertion into the access hub. Because the procedure to connect to a VAD is so common and simple, the risk associated with entry into a patient's vascular system has often been overlooked. Presently, the risk to hospitals and patients is a substantial function of the diligence of the clinician performing the connection, and this diligence is largely uncontrollable.

Disinfecting caps currently on the market are capable of only disinfecting one of the three types of luer fitting, namely female luer of needle-free connectors, female luer of stopcocks, and male luer connectors on intravenous injection sites. Currently, caps for male needleless connectors, female needleless connectors, intravenous (IV), and hemodialysis lines use different designs and are therefore limited to the types of connectors to which the cap can be attached. Prior disinfecting caps were designed to fit one type of connector only, and were specific to one particular size and/or shape of connector. Despite that certain disinfecting caps currently on the market are intended to be used with closed female luer on needleless connectors may generally fit open female luer on stopcocks as well, disinfecting caps currently on the market are not capable of disinfecting inner lumen of stopcocks. The disinfecting caps currently on the market are not capable of coupling onto both male and female connectors while disinfecting inner lumen of open female luer. Thus, there is a need for a disinfecting device capable of accommodating multiple types of connectors, including both female and male connectors, to streamline the disinfecting process.

SUMMARY

One aspect of the present disclosure pertains to a device for connection to a medical connector. The device, according to a second exemplary embodiment of the present disclosure, generally comprises a cap body, a coupling cylinder, a bulb compartment, a reageant compartment and a passageway connecting the bulb compartment to the reagent compartment.

The cap body includes a side wall having an outside surface and an inside surface, an open distal end, and a proximal end. The proximal end includes a proximal wall having an aperture. The side wall having a length $L_{O1}$ extending from the proximal end to the open distal end. The open distal end defines an end face.

In one or more embodiments, the coupling cylinder includes a side wall with an inner surface that mates to an outer threaded surface of a female connectors or a hemodialysis connectors, an outer surface that mates to a threaded surface of a collar on a male connector, a distal end and a proximal end.

In one or more embodiments, the bulb compartment is filled with air.

The reagent compartment defines a chamber containing a disinfectant or antimicrobial agent. The reagent compartment includes an exterior wall surface, an interior wall surface, an array of resealable pores densely integrated into the exterior wall surface and the interior wall surface of the reagent compartment, and a distal tip.

In one or more embodiments, the passageway is positioned in the aperture of the proximal wall.

In one or more embodiments, the distal end of the coupling cylinder includes an O-ring.

In one or more embodiments, the O-ring is made of an elastomeric material.

In one or more embodiments, the open distal end of the cap body is situated on approximately a same horizontal plane P as the distal tip of the reagent compartment or less than 8 mm away from the open distal end of the cap body in an initial state such that when a female luer connector or a male luer connector is engaged to the device, the reagent compartment is compressed and the reagent compartment retracts towards the proximal wall.

In one or more embodiments, the compression of the chamber releases the disinfectant or antimicrobial agent from the reagent compartment to disinfect the female luer connector or the male luer connector. In one or more embodiments, the disinfectant or antimicrobial agent is selected from the group consisting of isopropyl alcohol, ethanol, 2-propanol, butanol, methylparaben, ethylparaben, propylparaben, propyl gallate, butylated hydroxyanisole (BHA), butylated hydroxytoluene, t-butyl-hydroquinone, chloroxylenol, chlorohexidine, chlorhexidine diacetate, chlorohexidine gluconate, povidone iodine, alcohol, dichlorobenzyl alcohol, dehydroacetic acid, hexetidine, triclosan, hydrogen peroxide, colloidal silver, benzethonium chloride, benzalkonium chloride, octenidine, antibiotic, and mixtures thereof.

In one or more embodiments, the disinfectant or antimicrobial agent is a fluid or a gel.

In one or more embodiments, the female luer connector is selected from the group consisting essentially of needle-free connectors, stopcocks, and hemodialysis connectors.

In one or more embodiments, the male connector is an intravenous tubing end or stopcock.

In one or more embodiments, the device further includes a peelable seal on the open end of the cap body.

In one or more embodiments, the peelable seal may include an aluminum or multi-layer polymer film peel back top.

The device, according to a second exemplary embodiment of the present disclosure, generally comprises a cap body, a coupling cylinder, a bulb compartment, a reagent compartment and a passageway connecting the bulb compartment to the reagent compartment. The cap body includes a side wall having an outside surface and an inside surface, an open distal end, and a proximal end. The proximal end includes a proximal wall having an aperture. The side wall having a length $L_{O1}$ extending from the proximal end to the open distal end. The open distal end defines an end face.

In one or more embodiments, the coupling cylinder includes a side wall with an inner surface that mates to an outer threaded surface of a female connectors or a hemodialysis connectors, an outer surface that mates to a threaded surface of a collar on a male connector, a distal end and a proximal end. The coupling cylinder may be made of a semi-rigid material such as thermoplastic elastomer (TPE), a polypropylene (PP)/thermoplastic elastomer (TPE) blend, or polyethylene (PE)/thermoplastic elastomer (TPE) blend, or polypropylene (PP)/polyethylene (PE) material with a layer of thermoplastic elastomer (TPE) coat or other mixture of plastic and thermoplastic elastomer, thermoplastic elastomer (TPE) or rubber of similar elasticity. In one or more embodiments, the coupling cylinder may be made using a 2-shot molding process.

In one or more embodiments, the bulb compartment is filled with air.

The reagent compartment defines a chamber containing a disinfectant or antimicrobial agent. The reagent compartment includes an exterior wall surface, an interior wall surface, an array of resealable pores densely integrated into the exterior wall surface and the interior wall surface of the reagent compartment, and a distal tip.

In one or more embodiments, the passageway is positioned in the aperture of the proximal wall.

In one or more embodiments, the distal end of the coupling cylinder includes an O-ring.

In one or more embodiments, the O-ring is made of an elastomeric material.

In one or more embodiments, the side wall of the coupling cylinder includes one or more leaf springs.

In one or more embodiments, the open distal end of the cap body is situated on approximately a same horizontal plane P as the distal tip of the reagent compartment or less than 8 mm away from the open distal end of the cap body in an initial state such that when a female luer connector or a male luer connector is engaged to the device, the reagent compartment is compressed and the reagent compartment retracts towards the proximal wall.

In one or more embodiments, the compression of the chamber releases the disinfectant or antimicrobial agent from the reagent compartment to disinfect the female luer connector or the male luer connector. In one or more embodiments, the disinfectant or antimicrobial agent is selected from the group consisting of isopropyl alcohol, ethanol, 2-propanol, butanol, methylparaben, ethylparaben, propylparaben, propyl gallate, butylated hydroxyanisole (BHA), butylated hydroxytoluene, t-butyl-hydroquinone, chloroxylenol, chlorohexidine, chlorhexidine diacetate, chlorohexidine gluconate, povidone iodine, alcohol, dichlorobenzyl alcohol, dehydroacetic acid, hexetidine, triclosan, hydrogen peroxide, colloidal silver, benzethonium chloride, benzalkonium chloride, octenidine, antibiotic, and mixtures thereof.

In one or more embodiments, the disinfectant or antimicrobial agent is a fluid or a gel.

In one or more embodiments, the female luer connector is selected from the group consisting essentially of needle-free connectors, stopcocks, and hemodialysis connectors.

In one or more embodiments, the male connector is an intravenous tubing end or stopcock.

In one or more embodiments, the device further includes a peelable seal on the open end of the cap body.

In one or more embodiments, the peelable seal may include an aluminum or multi-layer polymer film peel back top.

The device, according to a third exemplary embodiment of the present disclosure, generally comprises a cap body, a coupling cylinder, a bulb compartment, a reagent compartment and a passageway connecting the bulb compartment to the reagent compartment. The reagent compartment defines a chamber containing a disinfectant or antimicrobial agent. The reagent compartment includes an exterior wall surface, an interior wall surface, an array of resealable pores densely integrated into the exterior wall surface and the interior wall surface of the reagent compartment, a permeable membrane disposed between the exterior wall surface and the interior wall surface of the reagent compartment, and a distal tip.

The cap body includes a side wall having an outside surface and an inside surface, an open distal end, and a proximal end. The side wall having a length $L_{O1}$ extending from the proximal end to the open distal end. The open distal end defines an end face.

In one or more embodiments, the coupling cylinder includes a side wall with an inner surface that mates to an outer threaded surface of a female connector or a hemodialysis connector, an outer surface which mates to a threaded surface of a collar on a male connector, a distal end and a proximal end.

In one or more embodiments, the bulb compartment is filled with air.

In one or more embodiments, the passageway positioned in the aperture of the proximal wall.

In one or more embodiments, the distal end of the coupling cylinder includes an O-ring.

In one or more embodiments, the O-ring is made of an elastomeric material.

In one or more embodiments, the side wall of the coupling cylinder includes one or more leaf springs.

In one or more embodiments, the open distal end of the cap body is situated on approximately a same horizontal plane P as the distal tip of the reagent compartment in an initial state.

In one or more embodiments, when a female luer connector or a male luer connector is engaged to the device of the present disclosure, the reagent compartment is compressed and the reagent compartment retracts towards the proximal wall.

In one or more embodiments, the compression of the chamber releases the disinfectant or antimicrobial agent from the reagent compartment to disinfect the female luer connector or the male luer connector. In one or more embodiments, the disinfectant or antimicrobial agent is selected from the group consisting of isopropyl alcohol, ethanol, 2-propanol, butanol, methylparaben, ethylparaben, propylparaben, propyl gallate, butylated hydroxyanisole (BHA), butylated hydroxytoluene, t-butyl-hydroquinone, chloroxylenol, chlorohexidine, chlorhexidine diacetate, chlorohexidine gluconate, povidone iodine, alcohol, dichlorobenzyl alcohol, dehydroacetic acid, hexetidine, triclosan, hydrogen peroxide, colloidal silver, benzethonium chloride, benzalkonium chloride, octenidine, antibiotic, and mixtures thereof.

In one or more embodiments, the disinfectant or antimicrobial agent is a fluid or a gel.

In one or more embodiments, the female luer connector is selected from the group consisting essentially of needle-free connectors, stopcocks, and hemodialysis connectors.

In one or more embodiments, the male connector is an intravenous tubing end or stopcock.

In one or more embodiments, the device further includes a peelable seal on the open end of the cap body. In one or more embodiments, the peelable seal includes an aluminum or multi-layer polymer film peel back top.

The device, according to a fourth exemplary embodiment of the present disclosure, generally comprises a cap body, a coupling cylinder having a side wall made of a thin sheet of metal, a bulb compartment, a reagent compartment and a passageway connecting the bulb compartment to the reagent compartment. In one or more embodiments, the passageway positioned in the aperture of the proximal wall. In one or more embodiments, the sheet metal of the coupling cylinder is perforated or meshed.

The cap body includes a side wall having an outside surface and an inside surface, an open distal end, and a proximal end. The proximal end includes a proximal wall. In one or more embodiments, the proximal wall includes an aperture. In one or more embodiments, the side wall has a length $L_{O1}$ extending from the proximal end to the open distal end. In one or more embodiments, the open distal end defines an end face.

In one or more embodiments, the side wall of the coupling cylinder includes an inner surface that mates to an outer threaded surface of a female connectors or a hemodialysis connectors, an outer surface that mates to a threaded surface of a collar on a male connector, a distal end and a proximal end.

In one or more embodiments, the bulb compartment filled with air;

The reagent compartment defines a chamber containing a disinfectant or antimicrobial agent. In one or more embodiments, the reagent compartment having an exterior wall surface, an interior wall surface, an array of resealable pores densely integrated into the exterior wall surface and the interior wall surface of the reagent compartment, and a distal tip.

BRIEF DESCRIPTION OF THE DRAWINGS

FIG. 11 illustrates a plan view of the device shown in FIG. 2 in connection with an open female luer connector according to the prior art;

FIG. 12 illustrates a plan view of the device shown in FIG. 2 in connection with a male luer connector according to the prior art;

DETAILED DESCRIPTION

Figure 1:
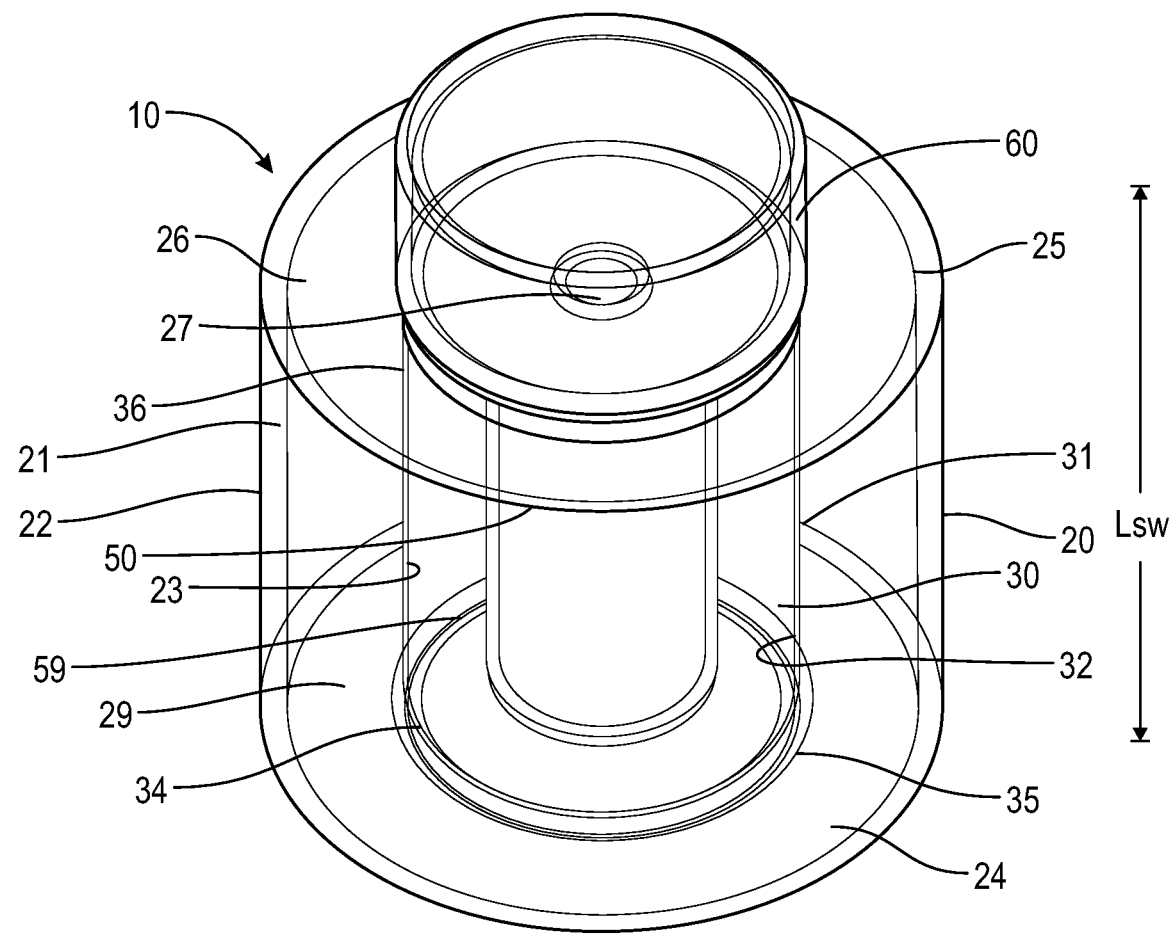
FIG. 1 illustrates a perspective view of a device according to a first embodiment.

Before describing several exemplary embodiments of the disclosure, it is to be understood that the disclosure is not limited to the details of construction or process steps set forth in the following description. The disclosure is capable of other embodiments and of being practiced or being carried out in various ways.

Embodiments of the disclosure pertain to a universal single-use device for connection to and disinfection of a male medical connector and a female medical connector, including male luer connectors and female luer connectors. In one or more embodiments, the universal single-use device comprises a disinfecting cap that can fit a broad range of luer fitting, including closed female luer, open female luer, and male luer fittings, while is capable of disinfecting the medical implement such as access ports including needleless connectors, male luer connectors on intravenous lines, male luer connectors on intravenous extensions, stopcocks, and hemodialysis connectors. The device contains a disinfectant or antimicrobial agent for disinfection. The device of the present disclosure allows the practitioner to streamline the disinfecting process.

With respect to terms used in this disclosure, the following definitions are provided.

As used herein, the use of "a," "an," and "the" includes the singular and plural.

As used herein, the term "catheter related bloodstream infection" or "CRBSI" refers to any infection resulting from the presence of a catheter or IV line.

In this disclosure, a convention is followed wherein the distal end of the device is the end closest to a patient and the proximal end of the device is the end away from the patient and closest to a practitioner.

The term "compressible" refers to a wall or container that is structured to be flexible enough to collapse at least partially into the inner chamber under manual depression. The shape and extent of the deformation will vary with the various configurations of the wall, container or chamber.

As used herein, the term "Luer connector" refers to a connection collar that is the standard way of attaching syringes, catheters, hubbed needles, IV tubes, etc. to each other. The Luer connector consists of male and female interlocking tubes, slightly tapered to hold together better with even just a simple pressure/twist fit. Luer connectors can optionally include an additional outer rim of threading, allowing them to be more secure. The Luer connector male end is generally associated with a flush syringe and can interlock and connect to the female end located on the vascular access device (VAD). A Luer connector comprises a distal end, a proximal end, an irregularly shaped outer wall, a profiled center passageway for fluid communication from the chamber of the barrel of a syringe to the hub of a VAD. A Luer connector also has a distal end channel that releasably attaches the Luer connector to the hub of a VAD, and a proximal end channel that releasably attaches the Luer connector to the barrel of a syringe.

Referring to FIG. 1, device 10 is used as a cap to be mounted onto connectors and is capable of being attached to connectors for a prolonged period of time. The device 10 for connection to a medical connector according to a first exemplary embodiment of the present disclosure generally comprises a cap body 20, a coupling cylinder 30, a bulb compartment 60, a reagent compartment 50 and a passageway 70 connecting the bulb compartment 60 to the reagent compartment 50. Cap body 20 serves as the scaffold of the device for mechanical support. The cap body includes a side wall 21 having an outside surface 22 and an inside surface 23, an open distal end 24, and a proximal end 25. The proximal end 25 of the cap body 20 includes a proximal wall 26 having an aperture 27. In one or more embodiments, the passageway is positioned in the aperture of the proximal wall.

The side wall 21 having a length $L_{sw}$ extending from the proximal end 25 to the open distal end 24. The open distal end 24 defines an end face. In one or more embodiments, as shown in FIG. 1, the cap body 20 is cylindrical in shape with an opening cavity 29. The opening cavity 29 of the cap body 20 allows access by connectors to a coupling cylinder 30 and antimicrobial reagent-containing compartment 50. The cap body 20 serves as the scaffold upon which the bulb compartment 60 and the reagent compartment 50 are attached. In one or more embodiments, the bulb compartment 60 and the reagent compartment 50 are attached via the aperture 27 located in the proximal wall 26 of proximal end 25 of the cap body 20. The cap body 20 also functions as a mechanical barrier to prevent inadvertent compression of reagent compartment 50. The cap body 20 is composed of rigid materials including polypropylene, high-density polyethylene (HDPE), polypropylene (PP)/thermoplastic elastomer (TPE) blend, or polyethylene (PE)/thermoplastic elastomer (TPE) blend, or polypropylene (PP)/polyethylene (PE) material with a layer of thermoplastic elastomer (TPE) coat. In one or more embodiments, the cap body may be made using a 2-shot molding process. In one or more embodiments, the device may further include a peelable seal on the open distal end 24 of the cap body 20. In one or more embodiments, the peelable seal may include an aluminum or multi-layer polymer film peel back top.

The coupling cylinder 30 is used to engage the threaded surface of luer connectors, including the threaded surface of needle-free connectors, threaded surface of the open female luer of stopcocks, and the threaded surface of the collar of male connectors. Coupling cylinder 30 is a cylindrical structure having a side wall 31 with an inner surface 32 that mates to an outer threaded surface of an open or closed female connector or a hemodialysis connectors, an outer surface that mates to a threaded surface of a collar on a male connector, an open distal end 34 and a proximal end 36. In one or more embodiments, the female luer connector may be a needle-free connector, stopcock, or hemodialysis connector. In one or more embodiments, the male connector may be an intravenous tubing end or stopcock.

The coupling cylinder may be made of a semi-rigid material such as thermoplastic elastomer (TPE), a polypropylene (PP)/thermoplastic elastomer (TPE) blend, or polyethylene (PE)/thermoplastic elastomer (TPE) blend, or polypropylene (PP)/polyethylene (PE) material with a layer of thermoplastic elastomer (TPE) coat or other mixture of plastic and thermoplastic elastomer, thermoplastic elastomer (TPE) or rubber of similar elasticity. In one or more embodiments, the coupling cylinder may be made using a 2-shot molding process.

In one or more embodiments, coupling cylinder 30 is concentrically placed within the cap body 20 and is attached to the proximal end 25 of the cap body 20. Coupling cylinder 30 is a deformable but structurally rigid coupler to match the geometry of different types of luer connectors. In one or more embodiments, coupling cylinder 30 is made of elastomeric materials. The coupling cylinder 30 has an opening cavity on the open distal end 34 on the same side as the opening cavity 29 of the cap body 20.

In one or more embodiments, the open distal end 34 of the coupling cylinder 30 includes an O-ring 35. In one or more embodiments, an O-ring 35 is integrated at the open distal end of the coupling cylinder 30 for a tight grip on connector surface. At the opening end of the cavity, the rim of the cylindrical coupler forms an O-ring 35 to enhance the tightness of the grip of the engagement between coupling cylinder 30 and connector surface. The O-ring 35 also serves the purpose of forming a seal to create an enclosed space between connector and the coupling cylinder 30. O-ring structure 35 at the open distal end 34 of the coupling cylinder 30 is able to seal any liquid reagent exiting from the reagent compartment upon mounting the device 10 onto connectors to prevent reagent leakage. In one or more embodiments, the O-ring 35 is made of an elastomeric material that is flexible and retains its original shape in an initial state. Upon insertion of a connector with the coupling cylinder 30, the O-ring 35 expands to accommodate the connector creating a tight seal around the connector. Upon removal of the connector, the O-ring 35 returns to its initial state.

In addition to luer engagement, another challenge for a disinfecting cap to effectively sterilize different types of connectors is a capability of conforming to surfaces of different geometry, including the flat surface of closed female luer that has septa embedded in the center, the cavity of open female luer of stopcocks, and the protrusion of male luer. To accomplish effective disinfection regardless the luer type, embodiments of the present disclosure have a compressible reagent compartment 50 that possesses the flexibility to conform to different types of surface that needs to be disinfected.

Reagent compartment 50 defines a chamber containing a disinfectant or antimicrobial agent. The reagent compartment 50 includes an exterior wall surface 52, an interior wall surface 54, an array of resealable pores densely integrated into the exterior wall surface 52 and the interior wall surface 54 of the reagent compartment 50, and a distal tip 58. The boundary material of reagent compartment 50 has a great number of densely integrated micro-sized or nano-sized pores 56 embedded in the polymer matrix of the reagent compartment 50 for reagent release. The boundary material of the sidewall 51 of reagent compartment is perforated by densely distributed auto-resealable pores. The pores 56 are opened when pressure is applied to the boundary sidewall 51. Such opening of pores 56 is reversible. The reagent compartment 50 is activatable by compressing the bulb compartment 60 that protrudes above the cap body 20. When the bulb compartment 60 is squeezed, an increase in pressure due to compressed air applies force to disinfectant or antimicrobial agent in the reagent compartment 50, resulting in the release of the disinfectant or antimicrobial agent through micro-sized or nano-sized pores 56 embedded in the polymer matrix of the reagent compartment 50. In one or more embodiments, the open distal end 24 of the cap body 20 is situated on approximately a same horizontal plane P as the distal tip 58 of the reagent compartment 50 or less than 8 mm away from the open distal end of the cap body in an initial state such that when a female luer connector or a male luer connector is engaged to the device 10, the reagent compartment 50 is compressed and the reagent compartment 50 retracts towards the proximal wall 26. The reagent compartment 50 is composed of a reversibly deformable material that is assembled onto the cap body 20 to fulfill the function to fit onto male or female luer connectors, to hold a volume of disinfectant or antimicrobial agent, to release the disinfectant or antimicrobial agent in a controllable manner, to seal the released disinfectant or antimicrobial agent in the confined spaced, and to mitigate ingress by blocking fluid paths. In one or more embodiments, the reagent compartment 50 is made of elastomeric materials.

The reagent compartment 50 contains disinfectant or antimicrobial agent has the capability of releasing the disinfectant or antimicrobial agent when compressed. The reagent compartment 50 takes the form of a cylinder with a conical distal tip, and constitutes a lower compressible compartment surrounded by the coupling cylinder 30. The reagent compartment 50 can serve as a protrusion to be inserted into an open female luer connector, meanwhile it possesses the ability to retract upon compressing against closed female luer connector and protrusion of a male luer connector. In one or more embodiments, the reagent compartment 50 is pre-filled or preloaded with a disinfectant or antimicrobial agent. In one or more embodiments, the reagent compartment 50 is connected to bulb compartment 60. In one or more embodiments, the boundary material of the reagent compartment 50 and bulb compartment 60 is composed of stretchable material such as elastomer (e.g. thermoplastic elastomer).

In one or more embodiments, either one or both of the reagent compartment 50 and the bulb compartment 60 can be compressed to apply pressure on the disinfectant or antimicrobial agent to facilitate the release of the disinfectant or antimicrobial agent. The reagent compartment 50 is also compressible and is automatically deformed upon mounting the device 10 onto a male or female connector to match the geometry of different types of male or female connectors. In one or more embodiments, the bulb compartment 60 is made of elastomeric materials. In one or more embodiments, the compression of the reagent compartment 50 releases the disinfectant or antimicrobial agent from the reagent compartment 50 to disinfect the female luer connector or the male luer connector.

Upon removal of pressure, due to elastic property of the boundary material, the pores automatically reseal themselves, recreating the barrier to prevent disinfectant or antimicrobial agent from leaking from the reagent compartment 50. Distal tip of the reagent compartment serves as a fluid path blocker to block the ingress of antimicrobial reagent when pressed against an entry port of a male luer connector upon mounting of the device 10 onto a male connector. In one or more embodiments, the distal tip of the reagent compartment 50 is conically shaped and is composed solidly of an elastomeric material for blocking the fluid path. The distal tip of the reagent compartment offers a mechanism to block the fluid path in closed female connector and male connector to prevent ingress of the disinfectant or antimicrobial agent into lumens of the respective female connector or male connectors. In one or more embodiments, reagent compartment 50 can be inserted into the inner lumen of stopcocks. The outer diameter of the distal tip of the reagent compartment 50 is compatible with that of open female luer connectors. Distal tip 58 can be compressed by male luer connectors and closed female luer connectors. Upon compression, enclosed disinfectant or antimicrobial agent retreats into the bulb compartment 60.

As will be discussed in detailed later in this disclosure, embodiment of the device of the present disclosure allows disinfection applicable to a variety of connectors. When the device 10 is mounted onto a closed female luer on a needle-free connector or a hemodialysis connector, the reagent compartment 50 is compressed against the end surface of the connector or the surface of a septum embedded in the connector. Such compression results in an increase in the intra-compartmental pressure, which in turn leads to the release of the disinfectant or antimicrobial agent to disinfect the end surface and luer threads of the needle-free connector. When the device 10 is mounted onto an open female luer, e.g. of a stopcock, the reagent compartment 50 having the shape similar to a male luer can be inserted complementarily into the open luer. Disinfectant or antimicrobial agent can be released into the inner lumen of stopcock by compressing the bulb compartment 60. When the cap is mounted onto a male connector, fluid path-blocking distal tip at the end of the reagent compartment 50 touches the luer port, blocking the port entrance to prevent subsequently released disinfectant or antimicrobial agent from accessing the inner lumen, thus mitigating the ingress of the disinfectant or antimicrobial agent. The compression of the reagent compartment 50 against the male luer results in the release of the antimicrobial for disinfection.

When reagent compartment 50 is deformed or the bulb compartment 60 is compressed, pressure is applied to disinfectant or antimicrobial agent, resulting in the discharge of disinfectant or antimicrobial agent from the reagent compartment into ex-compartmental area 59 to disinfect surface of a connector that the device 10 is attached to. The disinfectant or antimicrobial agent can be retained in the ex-compartmental space 59 by the O-ring seal 35. The reagent compartment 50 also has a sealing component at front end to afford capability of blocking fluid pathway to avoid ingress of antimicrobial reagent. In one or more embodiments, the device has one opening cavity and has a coupling mechanism that automatically fits different types of connectors with a simple mounting movement. The antimicrobial-preloaded compartment can be deformed to conform to different geometry of different types of connectors. The release of antimicrobial can be controlled by the deformation of either reagent compartment 50 or compressible bulb compartment 60. The released yet retained disinfectant or antimicrobial agent is capable of disinfecting connector ports for a prolonged period of time.

The reagent compartment 50 is designed to be compatible in interacting with various disinfectant or antimicrobial agent. In one or more embodiments, the disinfectant or antimicrobial reagent may include variations of alcohol or chlorhexidine. The disinfectant or antimicrobial reagents can be a fluid or a gel selected from the group consisting essentially of isopropyl alcohol, ethanol, 2-propanol, butanol, methylparaben, ethylparaben, propylparaben, propyl gallate, isopropanol, butylated hydroxyanisole (BHA), butylated hydroxytoluene, t-butyl-hydroquinone, chloroxylenol, chlorhexidine, chlorhexidine acetate, chloroxidine diacetate, chlorhexidine gluconate, povidone iodine, alcohol, dichlorobenzyl alcohol, dehydroacetic acid, hexetidine, triclosan, hydrogen peroxide, colloidal silver, benzethonium chloride, benzalkonium chloride, octenidine, octenidine dihydrochloride, antibiotic, and mixtures thereof. The reagent fills the reagent-containing compartment 50 which constitutes the lower compartment partially surrounded by a coupling cylinder 30, while leaving upper portion of the antimicrobial reagent-containing compartment 50 filled with air. The antimicrobial reagent-containing compartment 50 is composed of a stretchable material such as elastomer (e.g. thermoplastic elastomer).

In one or more embodiments, the reagent compartment 50 contains both air and liquid reagent where through force compression on the bulb compartment 60 or compression of the elastomeric material of the reagent compartment 50 during the insertion of a male or female connector results in air pressure on the liquid disinfectant or antimicrobial agent in the reagent compartment which causes an opening of the pores thus resulting in a release of anti-microbial reagent.

In one or more embodiments, as shown in FIG. 1, compressible bulb compartment 60 protrudes above the cap body 20. In one or more embodiments, the bulb compartment is filled with air or gas and the bulb compartment 60 is connected to the reagent compartment 50. When the reagent compartment 50 is compressed, the pressure in the bulb compartment 60 increases, resulting in the release of disinfectant or antimicrobial agent from the reagent compartment 50. The degree of pressure increase is determined by the elasticity of the boundary materials of the reagent compartment 50 and the bulb compartment 60. Bulb compartment 60 also provides additional control for modulating the pressure within the reagent compartment 50 and the bulb compartment 60. Manually compressing the bulb compartment 60 can allow additional release of disinfectant or antimicrobial agent from reagent compartment 50 to disinfect connectors.

In one or more embodiments, the bulb compartment 60 is made of elastomeric materials.

In one or more embodiments, the coupling cylinder 30, the reagent compartment 50 and the bulb compartment 60 are can be mechanically connected and can be formed as a single entity, as shown in FIG. 1. In one or more embodiment, the boundary of bulb compartment 60 and the reagent compartment 50 may be joined by ultrasonic welding or an adhesive. In an alternate embodiment, the coupling cylinder 30, the reagent compartment 50 and the bulb compartment 60 constitute three structurally distinct components.

Embodiments of the device 10 of the present disclosure are self-adaptive to different types of luer connectors due to due to a deformable coupling cylinder 30 that is capable of forming a seal onto both male and female luer connectors. The device 10 is also capable of deforming the shape of reagent compartment 50 to accommodate both male connectors, closed female connector, and open female connector, achieving effective disinfection not only on the outer surface of luer, but also inner lumen of open female luer.

In one or more embodiments, a removable seal attaches to the open end of the cap body to preserve the sterility of the distal tip, inner cavity and open distal end.

Referring to FIGS. 2-8, device 10 is used as a cap to be mounted onto connectors and is capable of being attached to connectors for a prolonged period of time. The device 10 for connection to a medical connector according to a first exemplary embodiment of the present disclosure generally comprises a cap body 20, a coupling cylinder 30, a bulb compartment 60, a reagent compartment 50 and a passageway 70 connecting the bulb compartment 60 to the reagent compartment 50. Cap body 20 serves as the scaffold of the device for mechanical support. The cap body includes a side wall 21 having an outside surface 22 and an inside surface 23, an open distal end 24, and a proximal end 25. The proximal end 25 of the cap body 20 includes a proximal wall 26 having an aperture 27. In one or more embodiments, the passageway is positioned in the aperture of the proximal wall.

Figure 2:
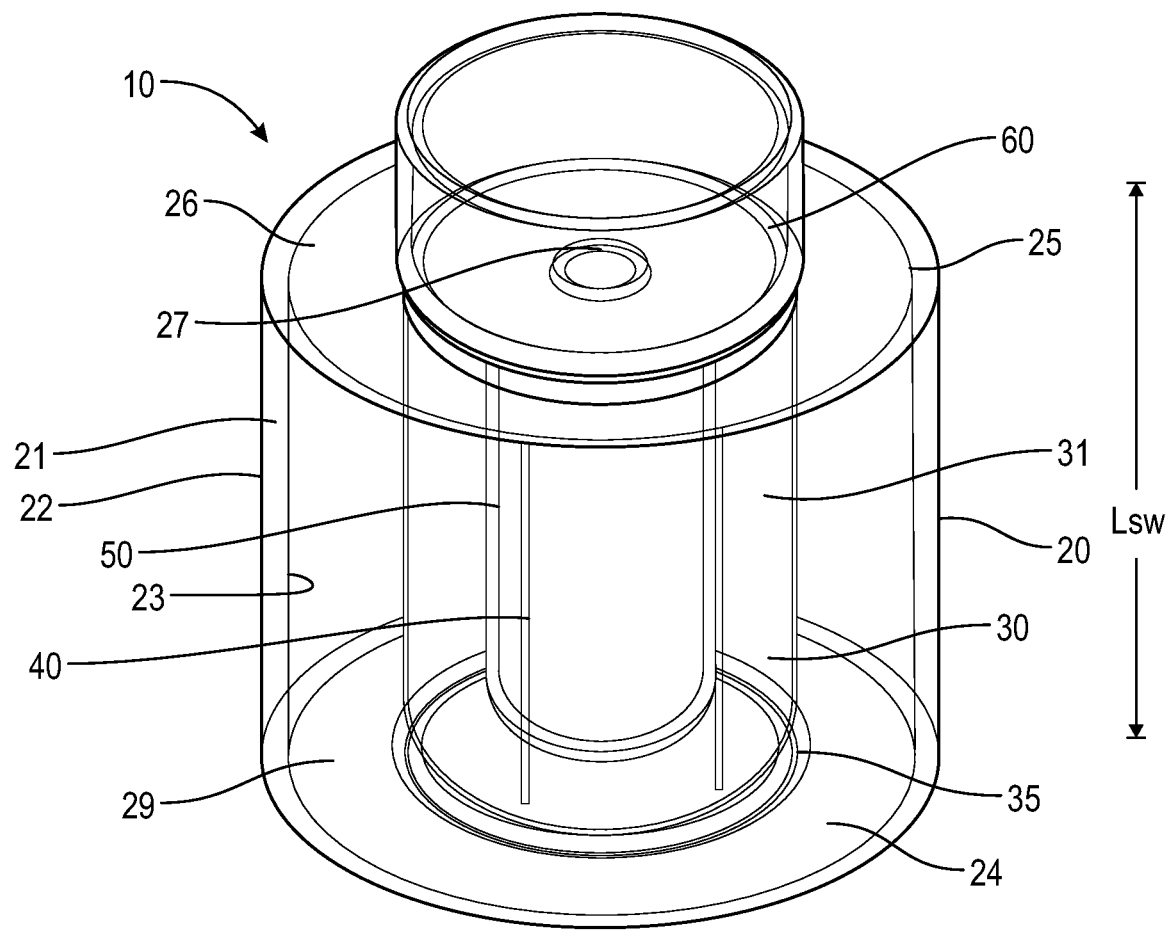
FIG. 2 illustrates a perspective view of a device according to a second embodiment.
Figure 3:
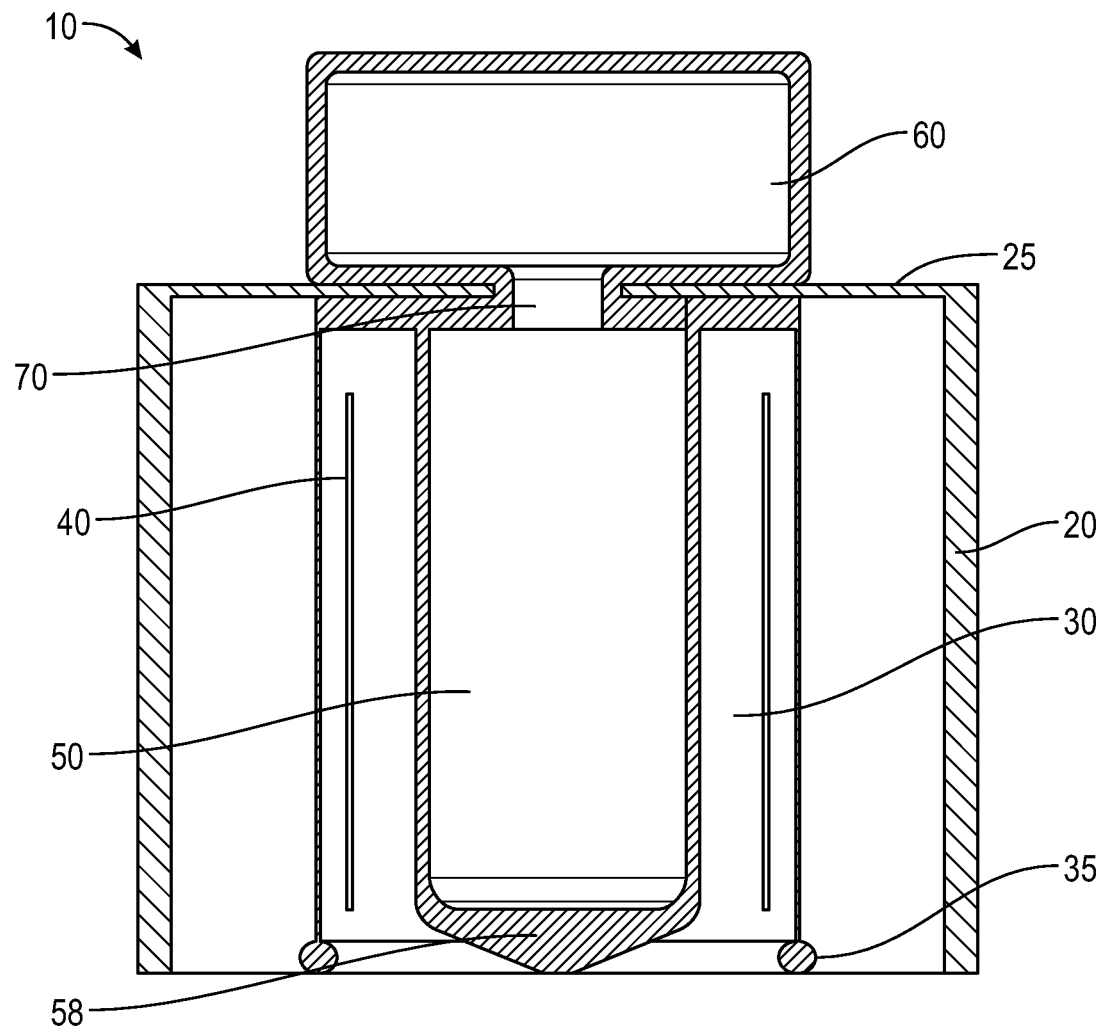
FIG. 3 illustrates a cross-sectional side view of the device shown in FIG. 2.
Figure 4:
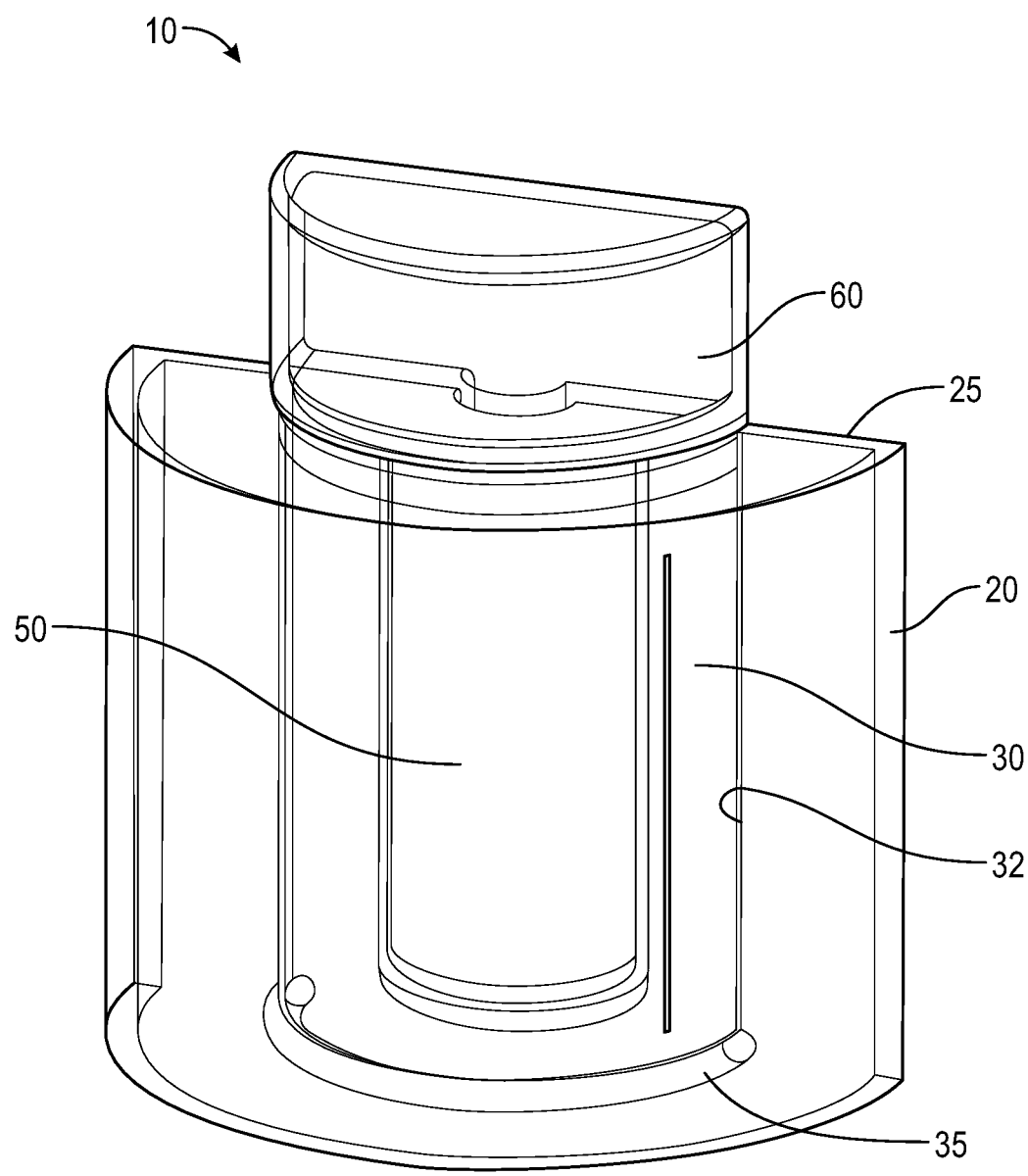
FIG. 4 illustrates a perspective cross-sectional side view of a device according to a second embodiment.
Figure 5:
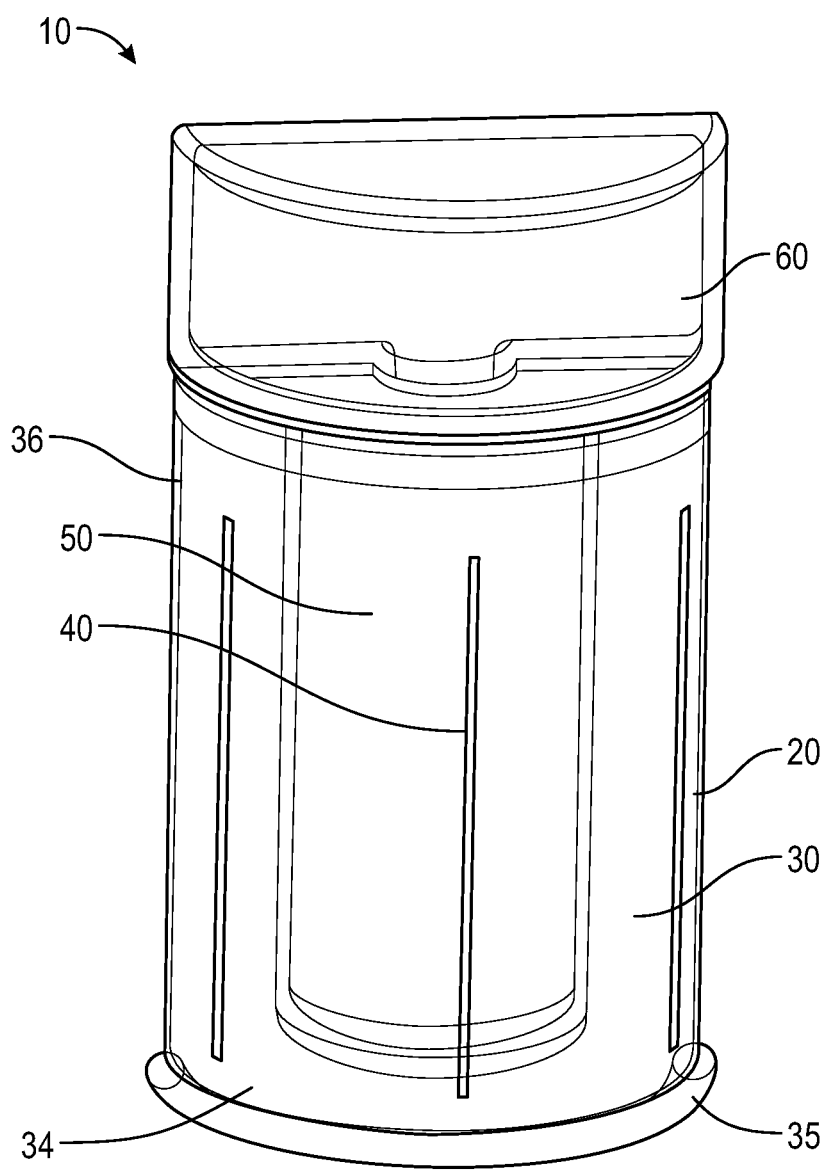
FIG. 5 illustrates a side view of the device according to a second embodiment.
Figure 6:
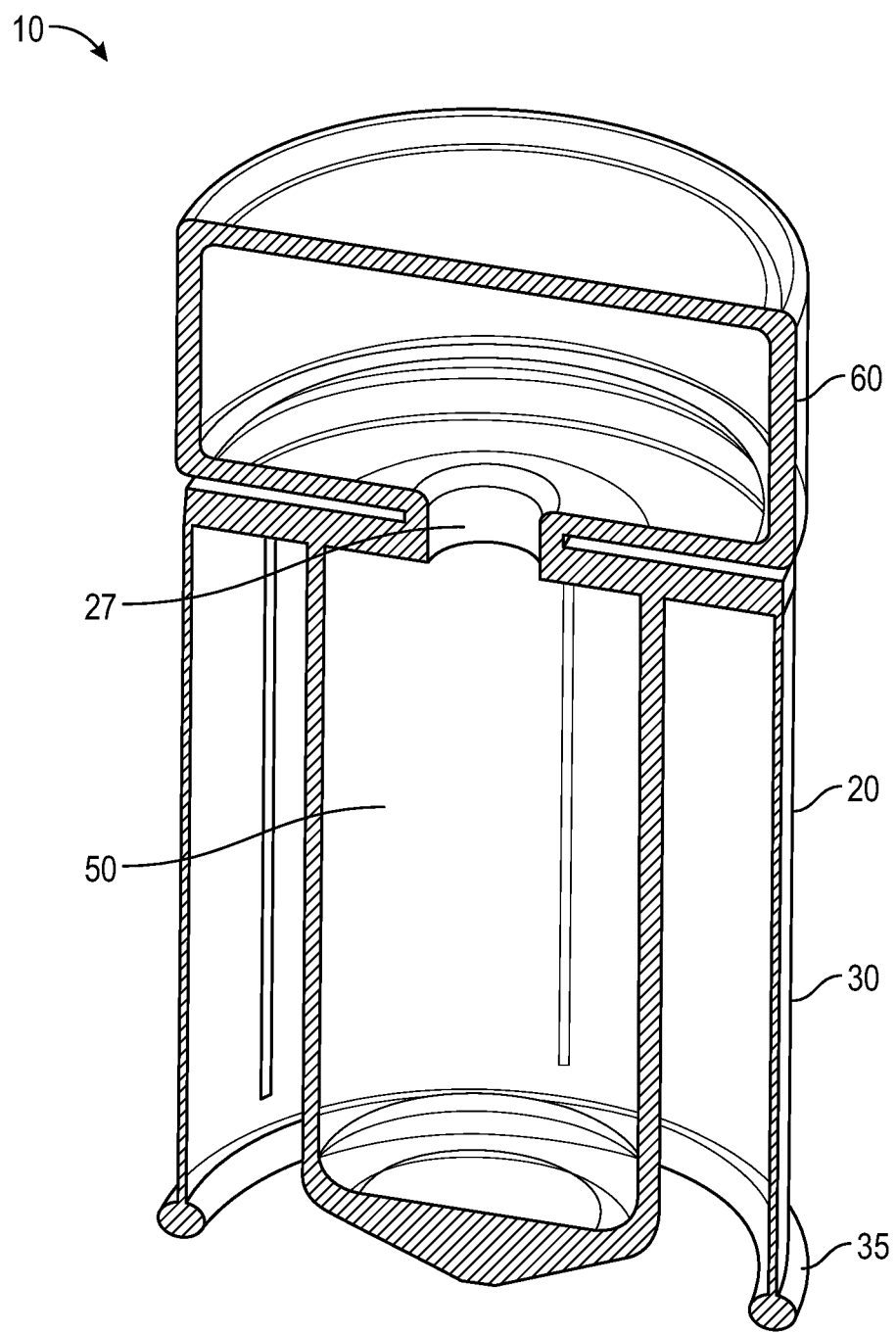
FIG. 6 illustrates cross-sectional side view of the device shown in FIG. 2.
Figure 7:
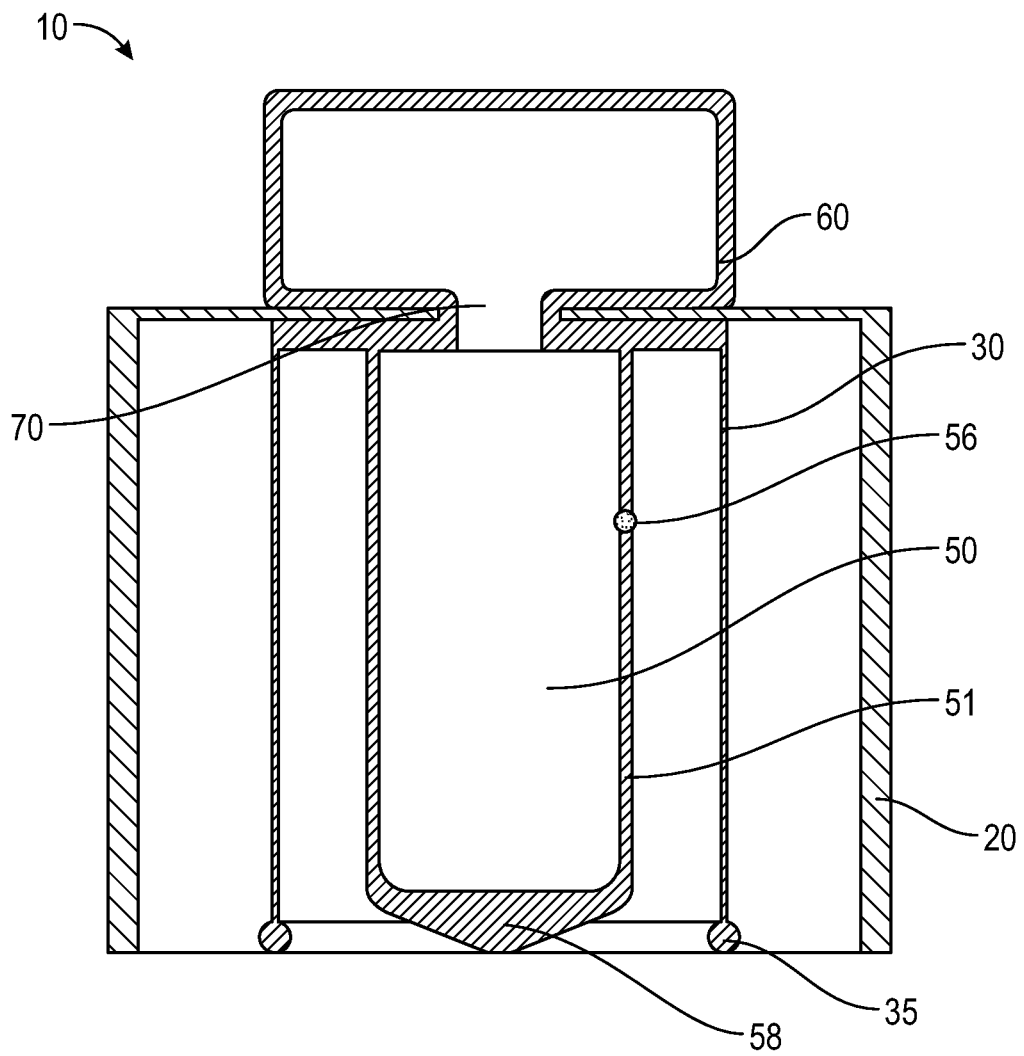
FIG. 7 illustrates a plan view of the device shown in FIG. 2.

The side wall 21 having a length $L_{sw}$ extending from the proximal end 25 to the open distal end 24. The open distal end 24 defines an end face. In one or more embodiments, as shown in FIGS. 2-4, the cap body 20 is cylindrical in shape with an opening cavity 29. The opening cavity 29 of the cap body 20 allows access by connectors to a coupling cylinder 30 and antimicrobial reagent-containing compartment 50, as shown in FIGS. 10-13. The cap body 20 serves as the scaffold upon which the bulb compartment 60 and the reagent compartment 50 are attached. In one or more embodiments, the bulb compartment 60 and the reagent compartment 50 are attached via the aperture 27 located in the proximal wall 26 of proximal end 25 of the cap body 20. The cap body 20 also functions as a mechanical barrier to prevent inadvertent compression of reagent compartment 50. The cap body 20 is composed of rigid materials including polypropylene, high-density polyethylene (HDPE), polypropylene (PP)/thermoplastic elastomer (TPE) blend, or polyethylene (PE)/thermoplastic elastomer (TPE) blend, or polypropylene (PP)/polyethylene (PE) material with a layer of thermoplastic elastomer (TPE) coat. In one or more embodiments, the cap body may be made using a 2-shot molding process. In one or more embodiments, the device may further include a peelable seal on the open distal end 24 of the cap body 20. In one or more embodiments, the peelable seal may include an aluminum or multi-layer polymer film peel back top.

The coupling cylinder may be made of a semi-rigid material such as thermoplastic elastomer (TPE), a polypropylene (PP)/thermoplastic elastomer (TPE) blend, or polyethylene (PE)/thermoplastic elastomer (TPE) blend, or polypropylene (PP)/polyethylene (PE) material with a layer of thermoplastic elastomer (TPE) coat or other mixture of plastic and thermoplastic elastomer, thermoplastic elastomer (TPE) or rubber of similar elasticity. In one or more embodiments, the coupling cylinder may be made using a 2-shot molding process.

The coupling cylinder 30 is used to engage the threaded surface of luer connectors, including the threaded surface of needle-free connectors, threaded surface of the open female luer of stopcocks, and the threaded surface of the collar of male connectors. Coupling cylinder 30 is a cylindrical structure having a side wall 31 with an inner surface 32 that mates to an outer threaded surface of an open or closed female connector or a hemodialysis connectors, an outer surface 33 that mates to a threaded surface of a collar on a male connector, an open distal end 34 and a proximal end 36. In one or more embodiments, the female luer connector may be a needle-free connector, stopcock, or hemodialysis connector. In one or more embodiments, the male connector may be an intravenous tubing end or stopcock.

In one or more embodiments, coupling cylinder 30 is concentrically placed within the cap body 20 and is attached to the proximal end 25 of the cap body 20. Coupling cylinder 30 is a deformable but structurally rigid coupler to match the geometry of different types of luer connectors. In one or more embodiments, coupling cylinder 30 is made of elastomeric materials. The coupling cylinder 30 has an opening cavity on the open distal end 34 on the same side as the opening cavity 29 of the cap body 20. In one or more embodiments, the coupling cylinder 30 is composed of a structure that combines the flexibility of elastomers and the rigidity of a metal material, affording the capability of geometrical compliance to different types of connectors, while maintaining a tight grip on connectors for prolonged disinfection. In one or more embodiments, one or more leaf springs 40 are integrated into the side wall 31 of the coupling cylinder 30 to afford mechanical strength to maintain the original form of sealing coupling cylinder 30 upon mounting onto male or female connectors and reacts against the deforming force applied by connectors. Leaf springs 40 may be embedded in the material of side wall 31 of the coupling cylinder 30, embedded in a groove in the material of side wall 31 of the coupling cylinder 30, or inserted during molding or attached through adhesive into the side wall 31 of the coupling cylinder 30. In one or more embodiment, leaf springs 40 are embedded longitudinally in the thin side wall 31 of the coupling cylinder 30 to afford rigidity and structural strength to maintain the shape integrity of the coupler when the cap is mounted onto the threaded surfaces of connectors. The leaf springs 40 can be made of rigid yet deformable materials, including thin sheets of stainless steel or metal alloy. The leaf springs 40 can take the form of rectangles with high geometrical aspect ratio. An array of 4 to 6 leaf springs 40 can be embedded into the wall of the coupling cylinder 30 with equal angular spread and the array can be axially symmetric about the central axis of the coupling cylinder 30.

In one or more embodiments, the open distal end 34 of the coupling cylinder 30 includes an O-ring 35. In one or more embodiments, an O-ring 35 is integrated at the open distal end of the coupling cylinder 30 for a tight grip on connector surface. At the opening end of the cavity, the rim of the cylindrical coupler forms an O-ring 35 to enhance the tightness of the grip of the engagement between coupling cylinder 30 and connector surface. The O-ring 35 also serves the purpose of forming a seal to create an enclosed space between connector and the coupling cylinder 30. O-ring structure 35 at the open distal end 34 of the coupling cylinder 30 is able to seal any liquid reagent exiting from the reagent compartment upon mounting the device 10 onto connectors to prevent reagent leakage. In one or more embodiments, the O-ring 35 is made of an elastomeric material that is flexible and retains its original shape in an initial state. Upon insertion of a connector with the coupling cylinder 30, the O-ring 35 expands to accommodate the connector creating a tight seal around the connector. Upon removal of the connector, the O-ring 35 returns to its initial state.

In addition to luer engagement, another challenge for a disinfecting cap to effectively sterilize different types of connectors is a capability of conforming to surfaces of different geometry, including the flat surface of closed female luer that has septa embedded in the center, the cavity of open female luer of stopcocks, and the protrusion of male luer. To accomplish effective disinfection regardless the luer type, embodiments of the present disclosure have a compressible reagent compartment 50 that possesses the flexibility to conform to different types of surface that needs to be disinfected.

Figure 8:
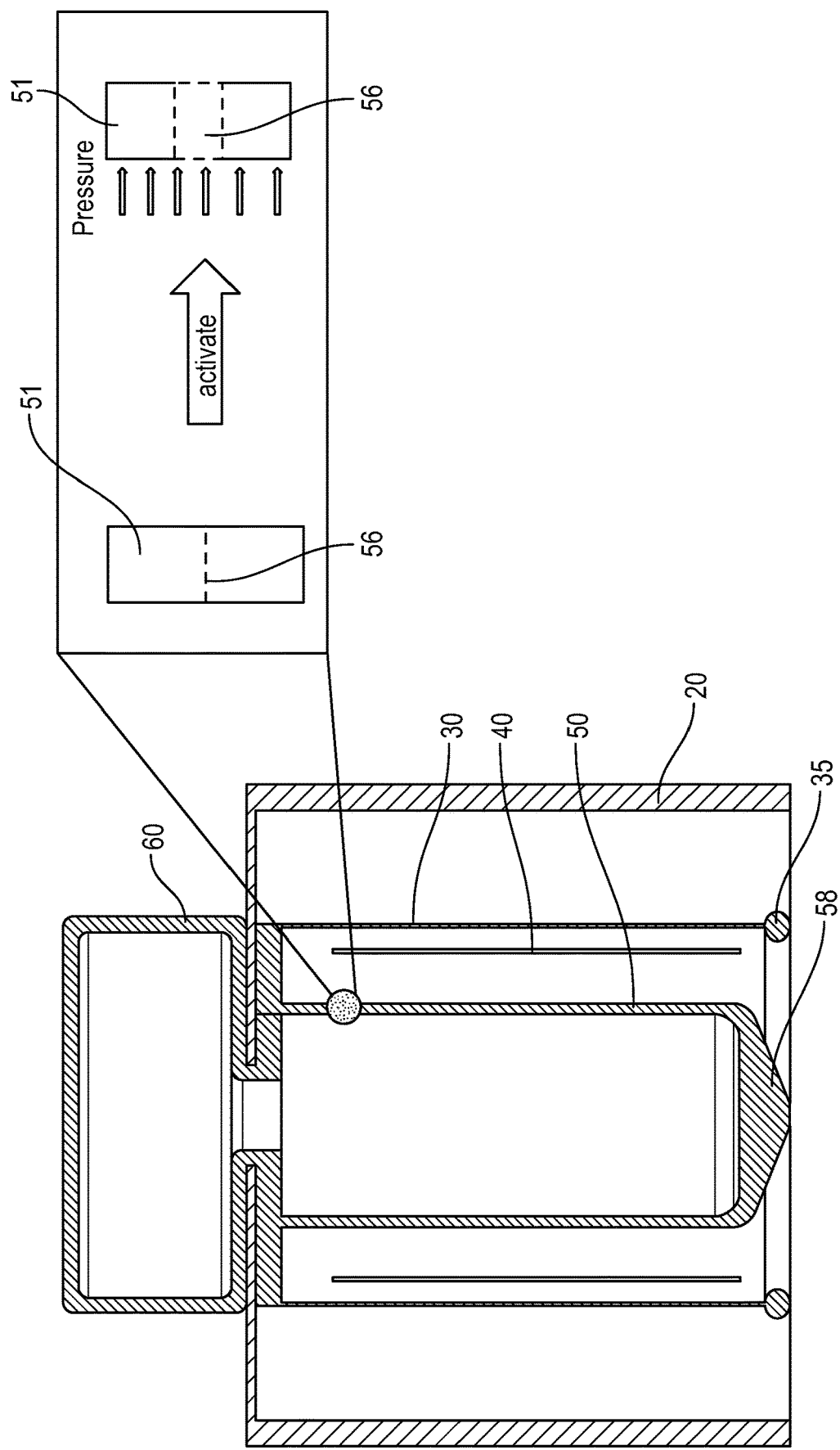
FIG. 8 illustrates a side view of the device shown in FIG. 2.
Figure 9:
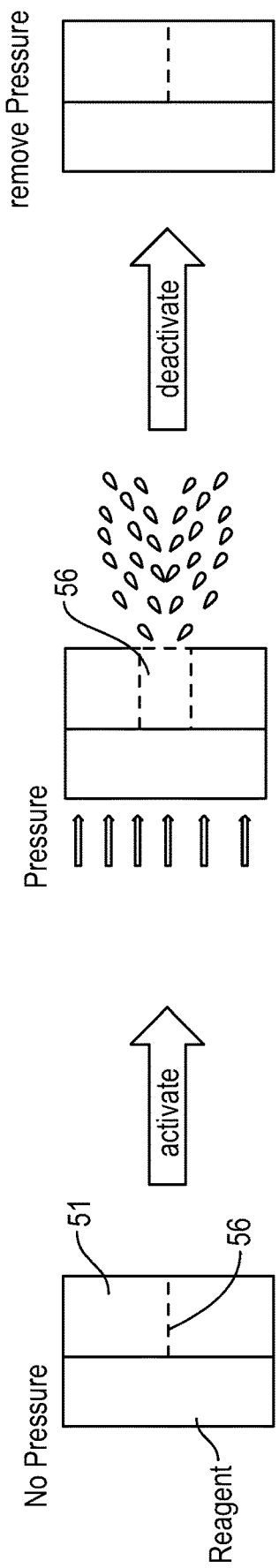
FIG. 9 illustrates a schematic view of wall of the reagent compartment of the device shown in FIG. 2.

Reagent compartment 50 defines a chamber containing a disinfectant or antimicrobial agent. The reagent compartment 50 includes an exterior wall surface 52, an interior wall surface 54, an array of resealable pores 56 densely integrated into the exterior wall surface 52 and the interior wall surface 54 of the reagent compartment 50, and a distal tip 58. The boundary material of reagent compartment 50 has a great number of densely integrated micro-sized or nano-sized pores 56 embedded in the polymer matrix of the reagent compartment 50 for reagent release. The boundary material of the sidewall 51 of reagent compartment is perforated by densely distributed auto-resealable pores. The pores 56 are opened when pressure is applied to the boundary sidewall 51, as shown in FIGS. 8-9. Such opening of pores 56 is reversible. The reagent compartment 50 is activatable by compressing the bulb compartment 60 that protrudes above the cap body 20. When the bulb compartment 60 is squeezed, an increase in pressure due to compressed air applies force to disinfectant or antimicrobial agent in the reagent compartment 50, resulting in the release of the disinfectant or antimicrobial agent through micro-sized or nano-sized pores 56 embedded in the polymer matrix of the reagent compartment 50. In one or more embodiments, the open distal end 24 of the cap body 20 is situated on approximately a same horizontal plane P as the distal tip 58 of the reagent compartment 50 in an initial state such that when a female luer connector or a male luer connector is engaged to the device 10, the reagent compartment 50 is compressed and the reagent compartment 50 retracts towards the proximal wall 26. The reagent compartment 50 is composed of a reversibly deformable material that is assembled onto the cap body 20 to fulfill the function to fit onto male or female luer connectors, to hold a volume of disinfectant or antimicrobial agent, to release the disinfectant or antimicrobial agent in a controllable manner, to seal the released disinfectant or antimicrobial agent in the confined spaced, and to mitigate ingress by blocking fluid paths. In one or more embodiments, the reagent compartment 50 is made of elastomeric materials.

As shown in FIGS. 9-12, the reagent compartment 50 containing disinfectant or antimicrobial agent has the capability of releasing the disinfectant or antimicrobial agent when compressed. The reagent compartment 50 takes the form of a cylinder with a conical distal tip 58, and constitutes a lower compressible compartment surrounded by the coupling cylinder 30. The reagent compartment 50 can serve as a protrusion to be inserted into an open female luer connector, meanwhile it possesses the ability to retract upon compressing against closed female luer connector and protrusion of a male luer connector. In one or more embodiments, the reagent compartment 50 is pre-filled or preloaded with a disinfectant or antimicrobial agent. In one or more embodiments, the reagent compartment 50 is connected to bulb compartment 60. In one or more embodiments, the boundary material of the reagent compartment 50 and bulb compartment 60 is composed of stretchable material such as elastomer (e.g. thermoplastic elastomer).

In one or more embodiments, either one or both of the reagent compartment 50 and the bulb compartment 60 can be compressed to apply pressure on the disinfectant or antimicrobial agent to facilitate the release of the disinfectant or antimicrobial agent. The reagent compartment 50 is also compressible and is automatically deformed upon mounting the device 10 onto a male or female connector to match the geometry of different types of male or female connectors. In one or more embodiments, the bulb compartment 60 is made of elastomeric materials. In one or more embodiments, the compression of the reagent compartment 50 releases the disinfectant or antimicrobial agent from the reagent compartment 50 to disinfect the female luer connector or the male luer connector.

Figure 10:
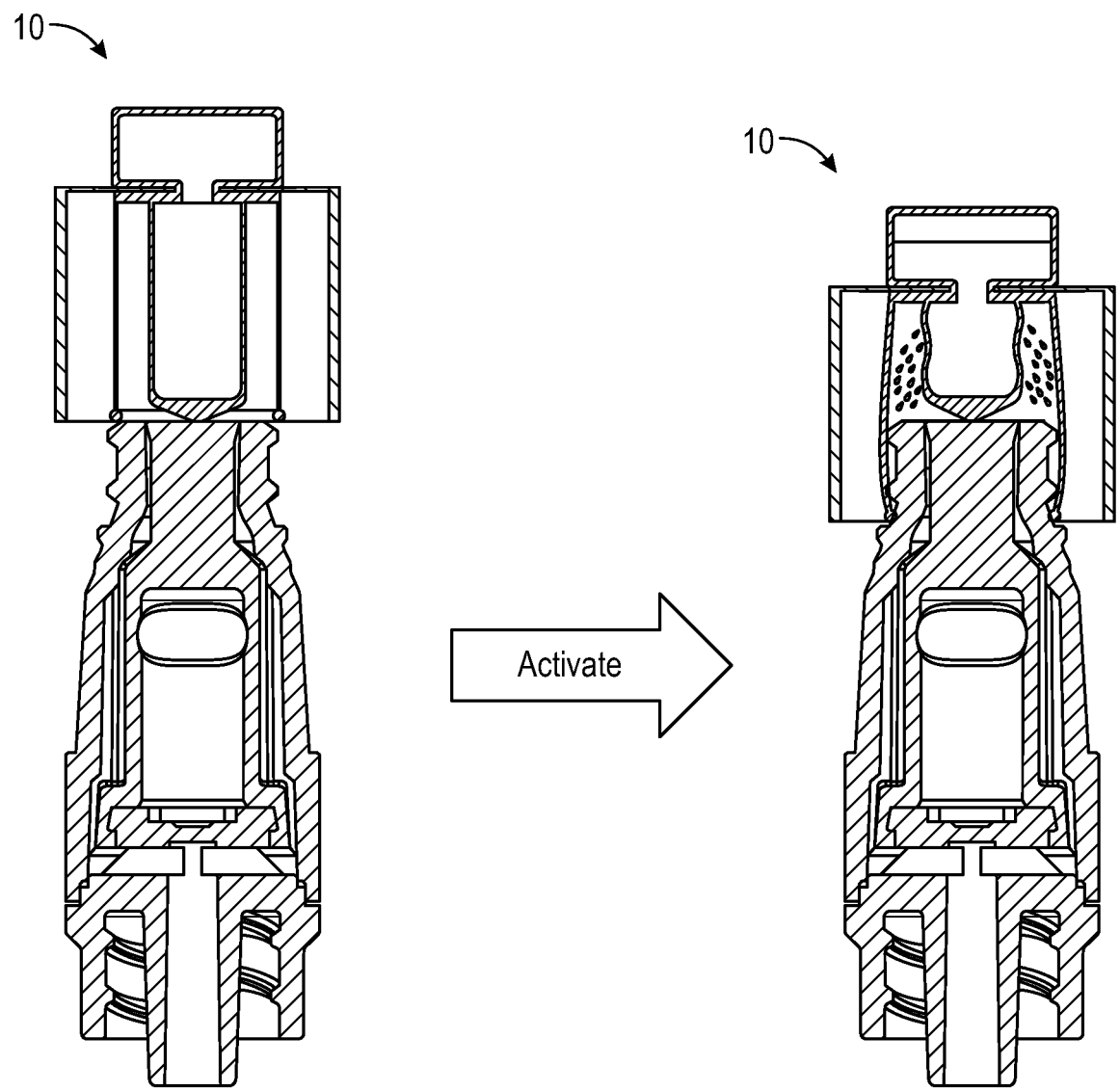
FIG. 10 illustrates a plan view of the device shown in FIG. 2 in connection with a closed female luer connector according to the prior art.

As shown in FIG. 9, upon removal of pressure, due to elastic property of the boundary material, the pores 56 automatically reseal themselves, recreating the barrier to prevent disinfectant or antimicrobial agent from leaking from the reagent compartment 50 as shown in FIG. 8-9. Distal tip 58 serves as a fluid path blocker to block the ingress of antimicrobial reagent when pressed against an entry port of a male luer connector upon mounting of the device 10 onto a male connector. The distal tip 58 of the reagent compartment 50 is conically shaped and is composed solidly of an elastomeric material for blocking the fluid path as shown in FIGS. 10-12. The distal tip 58 offers a mechanism to block the fluid path in closed female connector and male connector to prevent ingress of the disinfectant or antimicrobial agent into lumens of the respective female connector or male connectors. In one or more embodiments, reagent compartment 50 can be inserted into the inner lumen of stopcocks. The outer diameter of the distal tip 58 of the reagent compartment 50 is compatible with that of open female luer connectors. Distal tip 58 can be compressed by male luer connectors and closed female luer connectors. Upon compression, enclosed disinfectant or antimicrobial agent retreats into the bulb compartment 60.

Embodiment of the device of the present disclosure allows disinfection applicable to a variety of connectors. As shown in FIG. 10, when the device 10 is mounted onto a closed female luer on a needle-free connector or a hemodialysis connector, the reagent compartment 50 is compressed against the end surface of the connector or the surface of a septum embedded in the connector. Such compression results in an increase in the intra-compartmental pressure, which in turn leads to the release of the disinfectant or antimicrobial agent to disinfect the end surface and luer threads of the needle-free connector, as shown in FIG. 10. As shown in FIG. 11, when the device 10 is mounted onto an open female luer, e.g. of a stopcock, the reagent compartment 50 having the shape similar to a male luer can be inserted complementarily into the open luer. Disinfectant or antimicrobial agent can be released into the inner lumen of stopcock by compressing the bulb compartment 60, as shown in FIG. 11. As shown in FIG. 12, when the cap is mounted onto a male connector, fluid path-blocking distal tip 58 at the end of the reagent compartment 50 touches the luer port, blocking the port entrance to prevent subsequently released disinfectant or antimicrobial agent from accessing the inner lumen, thus mitigating the ingress of the disinfectant or antimicrobial agent. As shown in FIG. 12, the compression of the reagent compartment 50 against the male luer results in the release of the antimicrobial for disinfection.

When reagent compartment 50 is deformed or the bulb compartment 60 is compressed, pressure is applied to disinfectant or antimicrobial agent, resulting in the discharge of disinfectant or antimicrobial agent from the reagent compartment into ex-compartmental area 59 to disinfect surface of a connector that the device 10 is attached to. The disinfectant or antimicrobial agent can be retained in the ex-compartmental space 59 by the O-ring seal 35. The reagent compartment 50 also has a sealing component at front end to afford capability of blocking fluid pathway to avoid ingress of antimicrobial reagent. In one or more embodiments, the device has one opening cavity and has a coupling mechanism that automatically fits different types of connectors with a simple mounting movement. The antimicrobial-preloaded compartment can be deformed to conform to different geometry of different types of connectors. The release of antimicrobial can be controlled by the deformation of either reagent compartment 50 or compressible bulb compartment 60. The released yet retained disinfectant or antimicrobial agent is capable of disinfecting connector ports for a prolonged period of time.

The reagent compartment 50 is designed to be compatible in interacting with various disinfectant or antimicrobial agent. In one or more embodiments, the disinfectant or antimicrobial reagent may include variations of alcohol or chlorhexidine. The disinfectant or antimicrobial reagents can be a fluid or a gel selected from the group consisting essentially of isopropyl alcohol, ethanol, 2-propanol, butanol, methylparaben, ethylparaben, propylparaben, propyl gallate, isopropanol, butylated hydroxyanisole (BHA), butylated hydroxytoluene, t-butyl-hydroquinone, chloroxylenol, chlorohexidine, chlorhexidine acetate, chlorhexidine diacetate, chlorhexidine gluconate, povidone iodine, alcohol, dichlorobenzyl alcohol, dehydroacetic acid, hexetidine, triclosan, hydrogen peroxide, colloidal silver, benzethonium chloride, benzalkonium chloride, octenidine, octenidine dihydrochloride, antibiotic, and mixtures thereof. The reagent fills the reagent-containing compartment 50 which constitutes the lower compartment partially surrounded by a coupling cylinder 30, while leaving upper portion of the antimicrobial reagent-containing compartment 50 filled with air. The antimicrobial reagent-containing compartment 50 is composed of a stretchable material such as elastomer (e.g. thermoplastic elastomer).

In one or more embodiments, the reagent compartment 50 contains both air and liquid reagent where through force compression on the bulb compartment 60 or compression of the elastomeric material of the reagent compartment 50 during the insertion of a male or female connector results in air pressure on the liquid disinfectant or antimicrobial agent in the reagent compartment which causes an opening of the pores thus resulting in a release of anti-microbial reagent.

In one or more embodiments, compressible bulb compartment 60 protrudes above the cap body 20. In one or more embodiments, the bulb compartment is filled with air or gas and the bulb compartment 60 is connected to the reagent compartment 50 as shown in FIGS. 2-8. When the reagent compartment 50 is compressed, the pressure in the bulb compartment 60 increases, resulting in the release of disinfectant or antimicrobial agent from the reagent compartment 50. The degree of pressure increase is determined by the elasticity of the boundary materials of the reagent compartment 50 and the bulb compartment 60. Bulb compartment 60 also provides additional control for modulating the pressure within the reagent compartment 50 and the bulb compartment 60. Manually compressing the bulb compartment 60 can allow additional release of disinfectant or antimicrobial agent from reagent compartment 50 to disinfect connectors. In one or more embodiments, the bulb compartment 60 is made of elastomeric materials. As shown in shown in FIGS. 2-8, the bulb compartment 60 may include a thumb press 61 located at the proximal end of the device which may be manually depressed in the direction shown by arrow "A" in FIG. 11.

In one or more embodiments, the coupling cylinder 30, the reagent compartment 50 and the bulb compartment 60 are can be mechanically connected and can be formed as a single entity, as shown in FIG. 8. In one or more embodiment, the boundary of bulb compartment 60 and the reagent compartment 50 may be joined by ultrasonic welding or an adhesive. In an alternate embodiment, the coupling cylinder 30, the reagent compartment 50 and the bulb compartment 60 constitute three structurally distinct components.

Embodiments of the device 10 of the present disclosure are self-adaptive to different types of luer connectors due to due to a deformable coupling cylinder 30 that is capable of forming a seal onto both male and female luer connectors. The device 10 is also capable of deforming the shape of reagent compartment 50 to accommodate both male connectors, closed female connector, and open female connector, achieving effective disinfection not only on the outer surface of luer, but also inner lumen of open female luer.

In one or more embodiments, a removable seal attaches to the open end of the cap body to preserve the sterility of the distal tip 58, inner cavity and open distal end.

Figure 13:
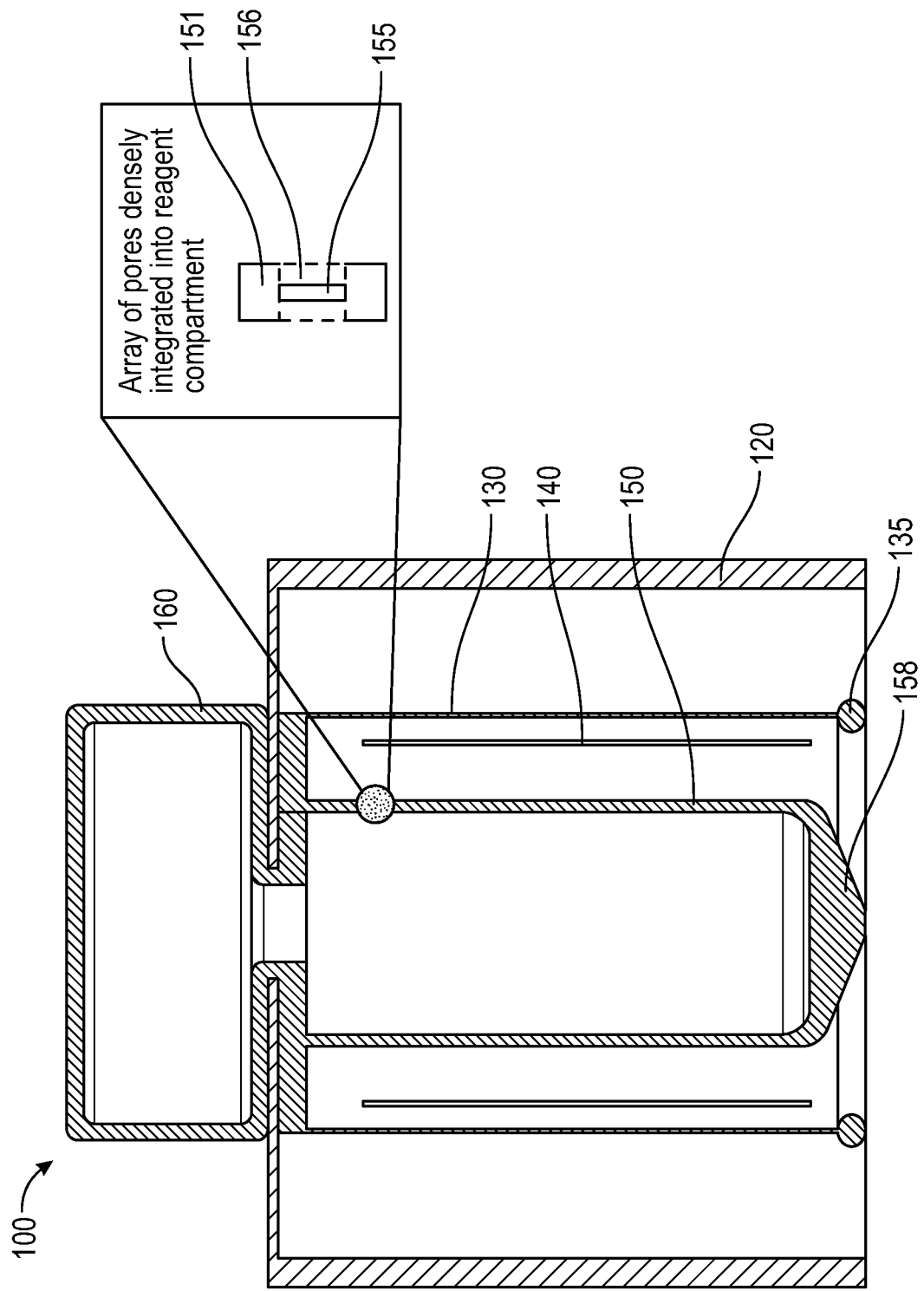
FIG. 13 illustrates a cross-sectional view of a device according to a third embodiment having a permeable membrane covering the boundary material of the compartment.
Figure 14:
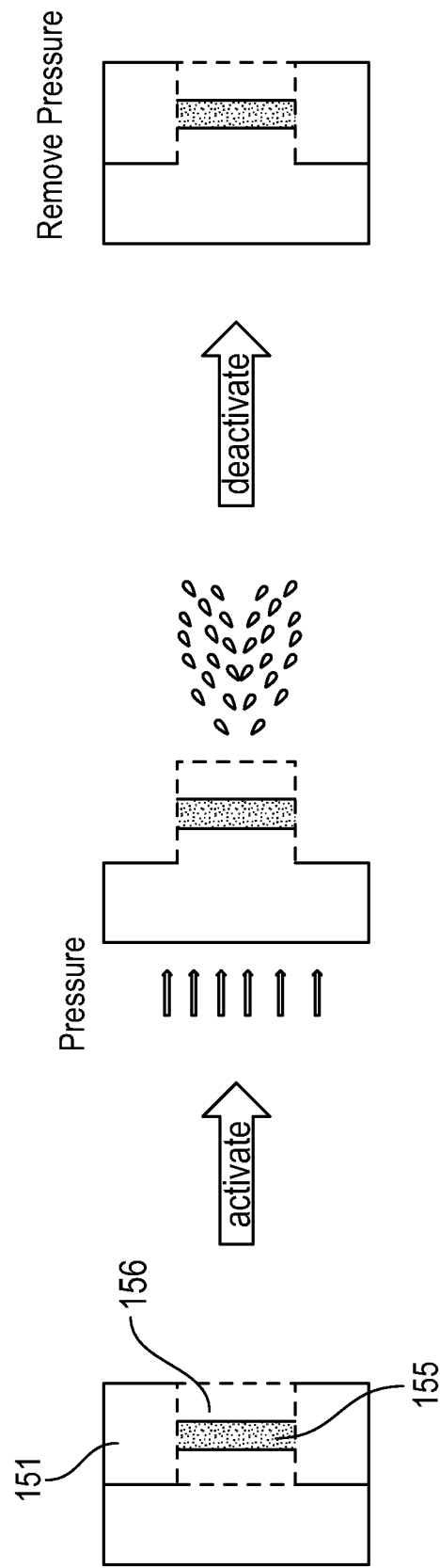
FIG. 14 illustrates a schematic view of wall of the reagent compartment of the device shown in FIG. 13.

As shown in FIG. 13, an alternative embodiment of present disclosure pertains to an alternate mechanism of release of the disinfectant or antimicrobial reagent. As shown in FIG. 13, device 100 includes a cap body 120, a coupling cylinder 130, a bulb compartment 160, a reagent compartment 150 and a passageway 170 connecting the bulb compartment 160 to the reagent compartment 150. Side wall 121 having an outside surface 122 and an inside surface 123, an open distal end 124, and a proximal end 125. The proximal end 125 of the cap body 120 includes a proximal wall 126 having an aperture 127. In one or more embodiments, the passageway is positioned in the aperture of the proximal wall. In one or more embodiments, the bulb compartment 160 and the reagent compartment 150 are attached via the aperture 127 located in the proximal wall 126 of proximal end 125 of the cap body 120. The cap body 120 also functions as a mechanical barrier to prevent inadvertent compression of reagent compartment 150. The cap body 120 is composed of rigid materials including polypropylene, high-density polyethylene (HDPE), polypropylene (PP)/thermoplastic elastomer (TPE) blend, or polyethylene (PE)/thermoplastic elastomer (TPE) blend, or polypropylene (PP)/polyethylene (PE) material with a layer of thermoplastic elastomer (TPE) coat. In one or more embodiments, the cap body may be made using a 2-shot molding process.

The side wall 121 having a length $L_{sw}$ extending from the proximal end 125 to the open distal end 124. The open distal end 124 defines an end face.

The coupling cylinder may be made of a semi-rigid material such as thermoplastic elastomer (TPE), a polypropylene (PP)/thermoplastic elastomer (TPE) blend, or polyethylene (PE)/thermoplastic elastomer (TPE) blend, or polypropylene (PP)/polyethylene (PE) material with a layer of thermoplastic elastomer (TPE) coat or other mixture of plastic and thermoplastic elastomer, thermoplastic elastomer (TPE) or rubber of similar elasticity. In one or more embodiments, the coupling cylinder may be made using a 2-shot molding process.

The coupling cylinder 130 is used to engage the threaded surface of luer connectors, including the threaded surface of needle-free connectors, threaded surface of the open female luer of stopcocks, and the threaded surface of the collar of male connectors. Coupling cylinder 130 is a cylindrical structure having a side wall 131 with an inner surface 132 that mates to an outer threaded surface of an open or closed female connector or a hemodialysis connectors, an outer surface 133 that mates to a threaded surface of a collar on a male connector, an open distal end 134 and a proximal end 136. In one or more embodiments, the female luer connector may be a needle-free connector, stopcock, or hemodialysis connector. In one or more embodiments, the male connector may be an intravenous tubing end or stopcock.

Reagent compartment 150 defines a chamber containing a disinfectant or antimicrobial agent. The reagent compartment 150 includes a sidewall 151 having an exterior wall surface 152, an interior wall surface 154, an array of resealable pores 156 densely integrated into the exterior wall surface 152 and the interior wall surface 154 of the reagent compartment 150, and a distal tip 158. A permeable membrane 155 disposed between the exterior wall surface 152 and the interior wall surface 154 of the reagent compartment 150.

A passageway 128 connects the bulb compartment 160 to the reagent compartment 150. In one or more embodiments, the passageway 128 is positioned in the aperture 127 of the proximal wall 126.

Figure 17:
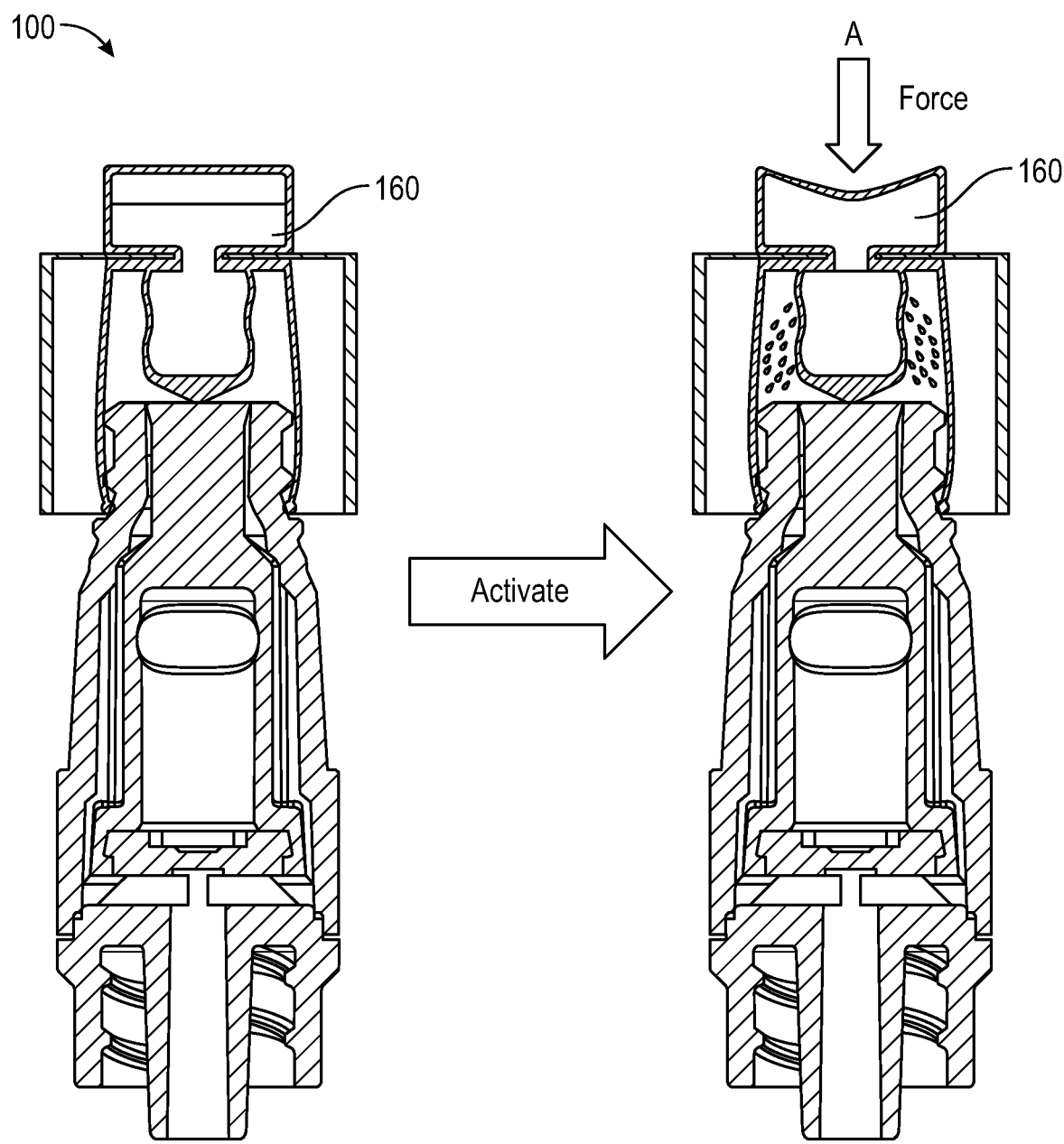
FIG. 17 illustrates a plan view of the device shown in FIG. 13 in connection with a female luer connector according to the prior art.
Figure 18:
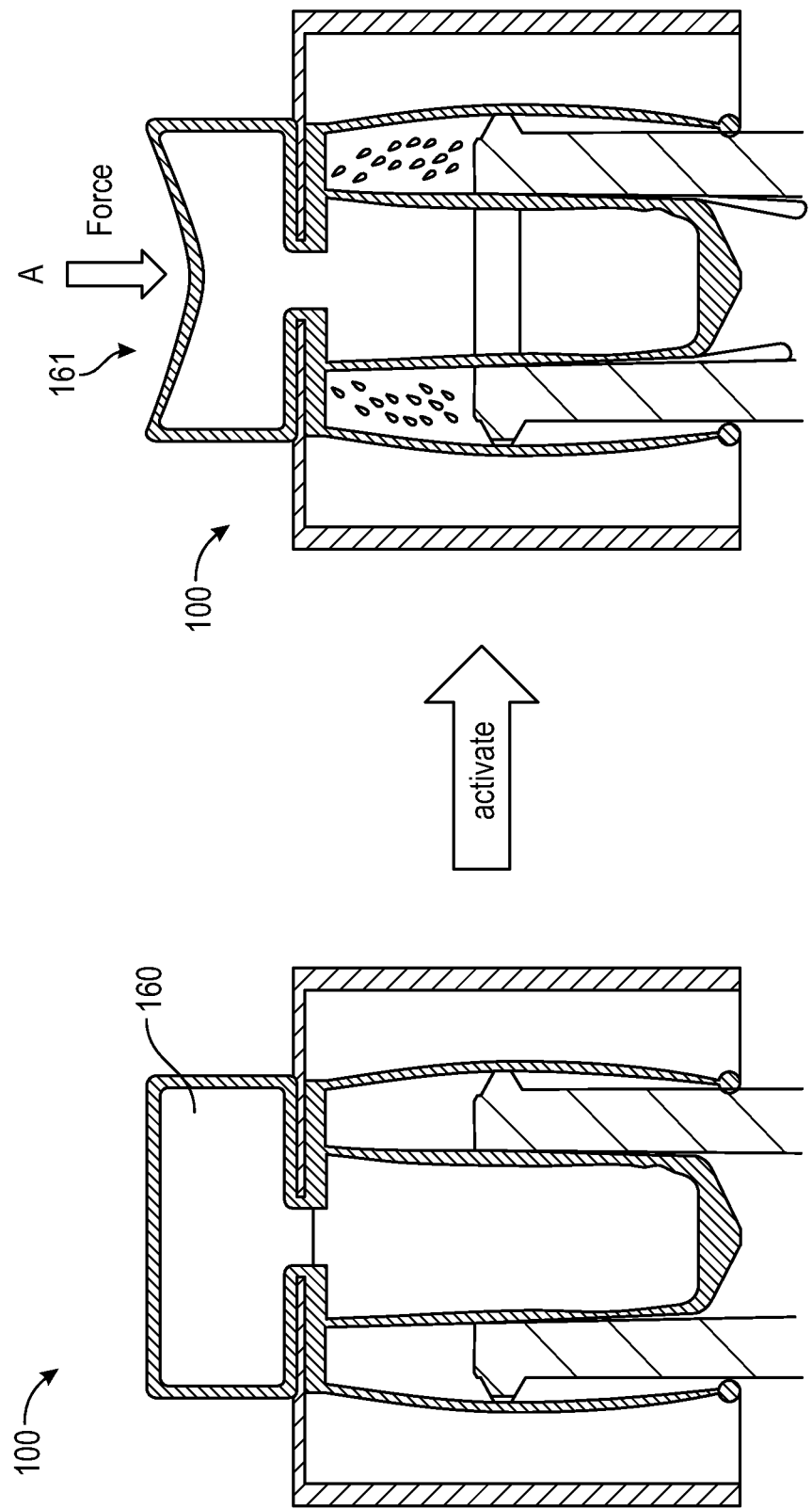
FIG. 18 illustrates a schematic view of wall of the reagent compartment of the device shown in FIG. 17.
Figure 19:
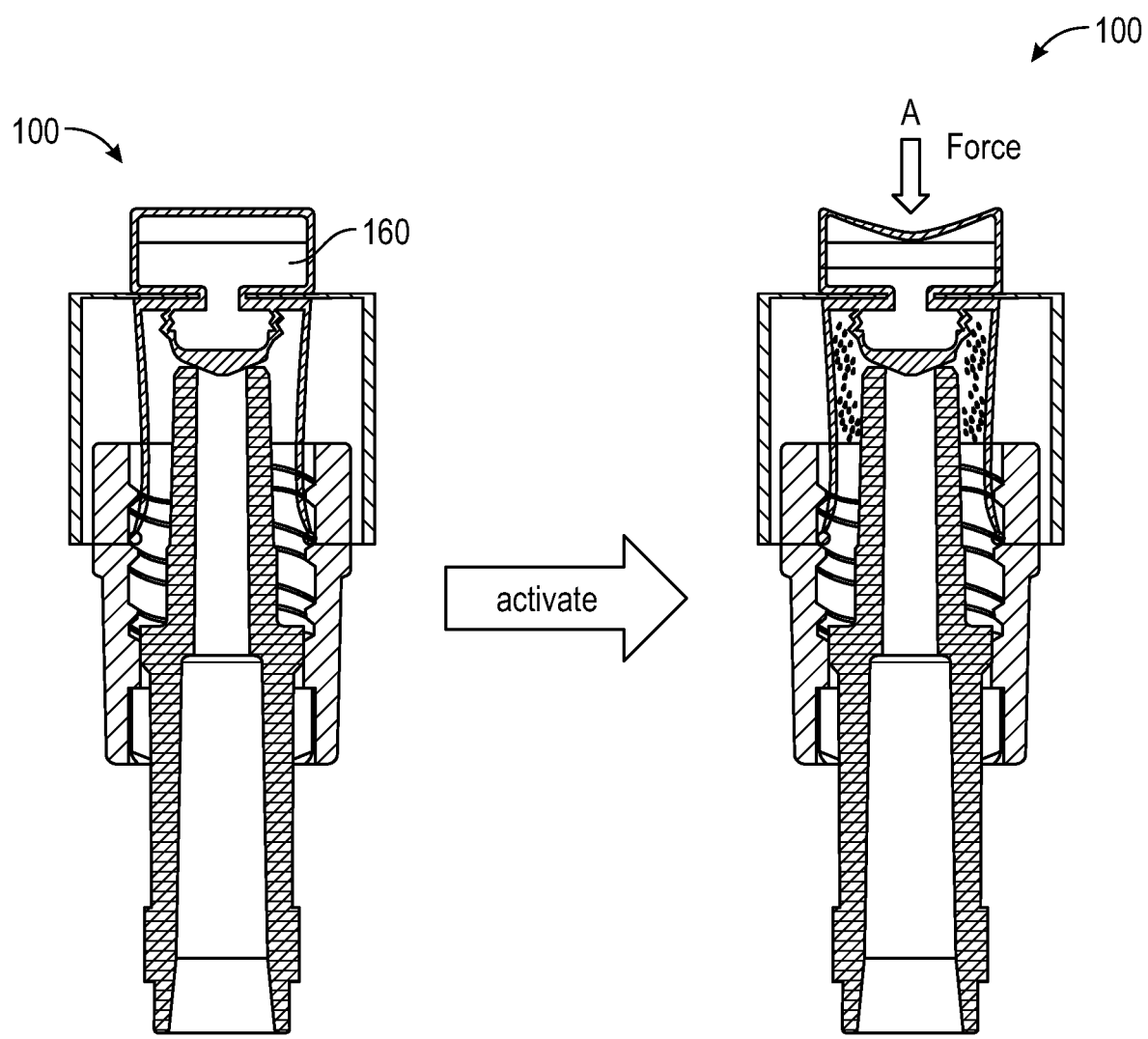
FIG. 19 illustrates a plan view of the device shown in FIG. 13 in connection with a male luer connector according to the prior art.

Sidewall 151 of the reagent compartment 150 is perforated by densely distributed micro-sized or nano-sized pores 156 densely integrated into the exterior wall surface 152 and the interior wall surface 154 of the reagent compartment 150. The pores 156 are covered by a layer of permeable membrane 155 that can either form a separate layer attached to the interior wall surface 154 of the reagent compartment, or be embedded into the cylindrical side wall 151 as an integrated material. The combination of the permeable membrane 155 and the pores 156 allows for the dispensing of disinfectant or antimicrobial agent when the pressure within the reagent compartment 150 is increased above a threshold as shown in FIGS. 14-19. The permeable membrane 155 adds an additional mechanism of control on the rate of disinfectant or antimicrobial agent release because the threshold pressure can be determined by adjusting the permeability of the permeable membrane material. For example, the threshold can be modulated high enough so the antimicrobial is not activated until the bulb compartment is manually compressed as shown in FIGS. 17-19.

Permeable membrane 155 is composed of a material with holes that are not completely removed so pores 156 open when pressure is applied. Pores 156 are micron holes coated by layer of permeable membrane 155 with very small scale creases where liquid disinfectant or antimicrobial agent can seep out. In one or more embodiment, the micron holes of the pores 156 are on a 100 micron scale. In one or more embodiment, the micron holes of the pores 156 are on a 100 nanometers scale. In one or more embodiment, after pressure is removed, holes in pores 156 remain open creating actual channel and are not resealable. In one or more embodiments, the pores are covered with a fiber mesh or filter material. In one or more embodiment, the permeable membrane after apply pressure, liquid penetrates without pressure, and forms a barrier because the small pore membrane is covered with a fiber mesh or filter material.

Figure 15:
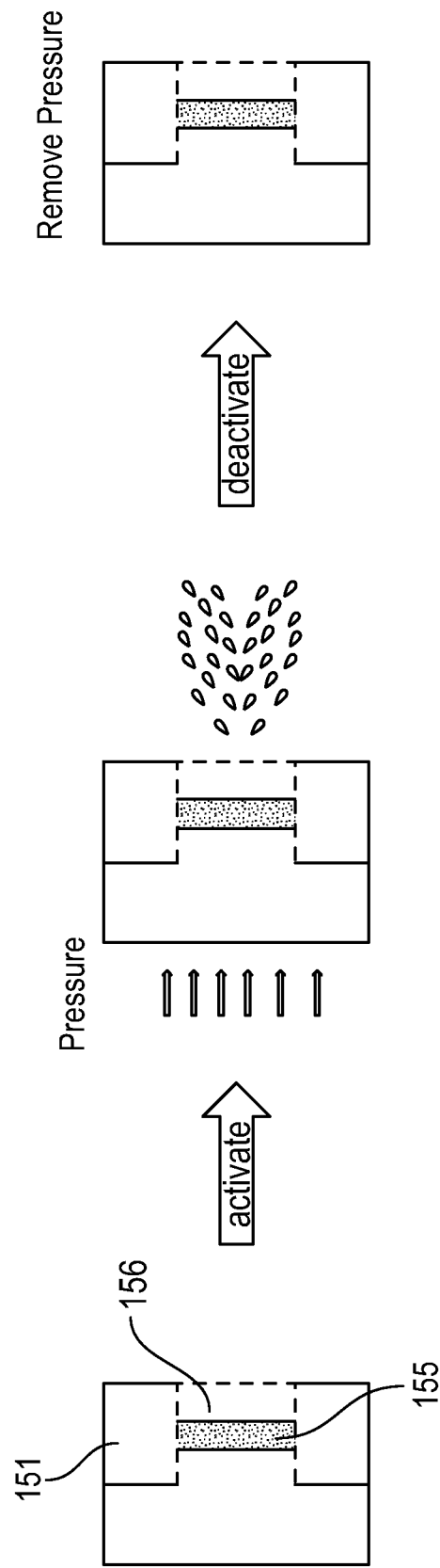
FIG. 15 illustrates a schematic view of wall of the reagent compartment of the device shown in FIG. 13.
Figure 16:
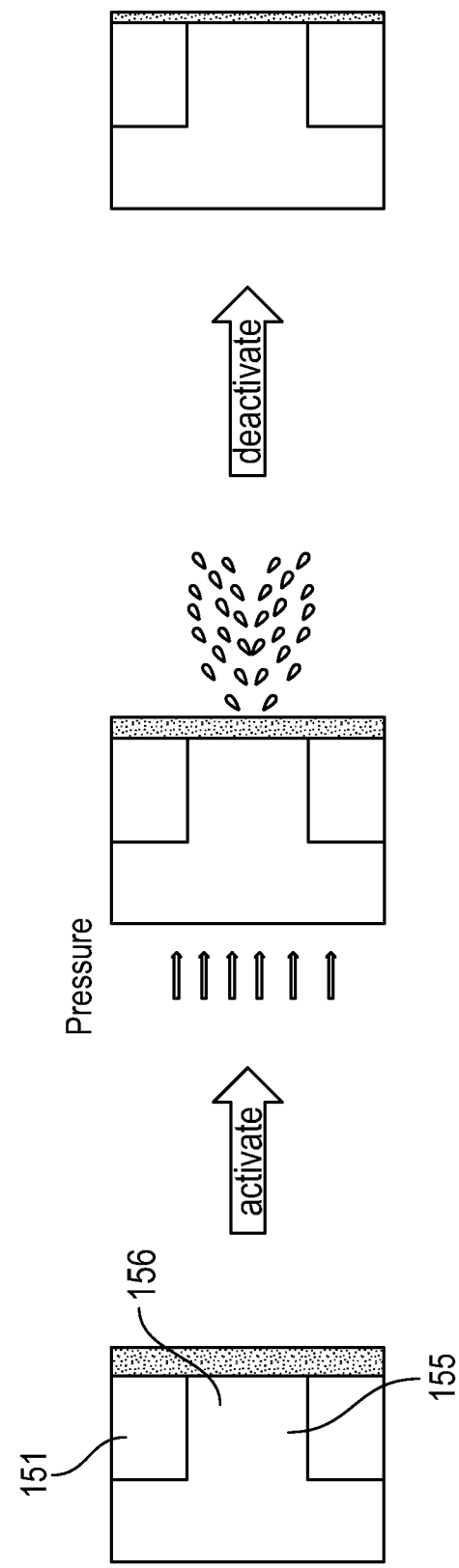
FIG. 16 illustrates a schematic view of wall of the reagent compartment of the device shown in FIG. 13.

The boundary material of reagent compartment 150 has a great number of micro-sized or nano-sized pores 156 embedded in the polymer matrix. Permeable membrane 155 is either attached to the compartment boundary as a separate layer or embedded into the boundary material to serve as a barrier to prevent enclosed liquid from leaking. In one or more embodiments, as shown in FIG. 15, the permeable membrane has smaller pores than the pores of the reagent compartment material. In one or more embodiments, the permeable membrane 155 is bonded over the reagent compartment 150. Permeable membrane 155 with smaller sized pores 156 (nano-pores) or a thin-layer of deposited material permeable to water.

In one or more embodiments, compressible bulb compartment 160 protrudes above the cap body 120. In one or more embodiments, the bulb compartment is filled with air or gas and the bulb compartment 160 is connected to the reagent compartment 150 as shown in FIG. 13. When the reagent compartment 150 is compressed, the pressure in the bulb compartment 160 increases, resulting in the release of disinfectant or antimicrobial agent from the reagent compartment 150. The degree of pressure increase is determined by the elasticity of the boundary materials of the sidewall and permeable membrane of the reagent compartment 150 and the bulb compartment 160. Bulb compartment 160 also provides additional control for modulating the pressure within the reagent compartment 150 and the bulb compartment 160. Manually compressing the bulb compartment 160 can allow additional release of disinfectant or antimicrobial agent from reagent compartment 150 to disinfect connectors. In one or more embodiments, the bulb compartment 160 is made of elastomeric materials. As shown in shown in FIG. 13, the bulb compartment 160 may include a thumb press 161 located at the proximal end of the device which may be manually depressed in the direction shown by arrow "A" in FIGS. 17-19.

The reagent compartment 150 is activated by compressing the upper bulb compartment 160 that protrudes above the cap body 120. In one or more embodiments, bulb compartment 260 is filled with air. When the bulb compartment 160 is squeezed, the increase in pressure due to compression of the air applies force to liquid disinfectant or antimicrobial agent in the reagent compartment 150, resulting in the release of the liquid disinfectant or antimicrobial agent through permeable membrane 155.

Reagent compartment 150 can be inserted into the inner lumen of stopcocks. Its outer diameter is compatible with that of open female luers. It can be compressed by male luer and closed female luer. FIGS. 17-18 illustrates the device shown in FIG. 13 in connection with a female luer connector according to the prior art. FIG. 19 illustrates a plan view of the device shown in FIG. 13 in connection with a male luer connector according to the prior art. Upon compression, enclosed fluid retreats into the bulb compartment 160.

The reagent compartment 150 is designed to be compatible in interacting with various disinfectant or antimicrobial agent. In one or more embodiments, the disinfectant or antimicrobial reagent may include variations of alcohol or chlorhexidine. The disinfectant or antimicrobial reagents can be a fluid or a gel selected from the group consisting essentially of isopropyl alcohol, ethanol, 2-propanol, butanol, methylparaben, ethylparaben, propylparaben, propyl gallate, isopropanol, butylated hydroxyanisole (BHA), butylated hydroxytoluene, t-butyl-hydroquinone, chloroxylenol, chlorohexidine, chlorhexidine acetate, chlorhexidine diacetate, chlorhexidine gluconate, povidone iodine, alcohol, dichlorobenzyl alcohol, dehydroacetic acid, hexetidine, triclosan, hydrogen peroxide, colloidal silver, benzethonium chloride, benzalkonium chloride, octenidine, octenidine dihydrochloride, antibiotic, and mixtures thereof. The reagent fills the reagent-containing compartment 150 which constitutes the lower compartment partially surrounded by a coupling cylinder 130, while leaving upper portion of the antimicrobial reagent-containing compartment 150 filled with air. In one or more embodiments, the antimicrobial reagent-containing compartment 150 is composed of a stretchable material such as elastomer, e.g. thermoplastic elastomer.

Coupling cylinder 130 is a cylindrical structure with opening at the bottom. The inner surface matches the outer threaded surface of open or closed female connectors, and hemodialysis connectors. The outer surface matches the threaded surface of the collar on male connectors.

In one or more embodiments, one or more leaf springs 140 are integrated into the side wall 131 of the coupling cylinder 130 to afford mechanical strength to maintain the original form of sealing coupling cylinder 130 upon mounting onto male or female connectors and reacts against the deforming force applied by connectors. Leaf springs 140 may be embedded in the material of side wall 131 of the coupling cylinder 130, embedded in a groove in the material of side wall 131 of the coupling cylinder 130, or inserted during molding or attached through adhesive into the side wall 131 of the coupling cylinder 130. The leaf springs 140 can be made of rigid yet deformable materials, including thin sheets of stainless steel or metal alloy. The leaf springs 140 can take the form of rectangles with high geometrical aspect ratio. An array of 4 to 6 leaf springs 140 can be embedded into the wall of the coupling cylinder 130 with equal angular spread and the array can be axially symmetric about the central axis of the coupling cylinder 130.

O-ring structure 135 at the open distal end 134 of the coupling cylinder 130 is able to seal the liquid disinfectant or antimicrobial agent upon mounting the device 100 onto connectors to prevent leakage of the disinfectant or antimicrobial agent. In one or more embodiments, O-ring 135 is integrated at the open distal end of the coupling cylinder 130 for a tight grip on connector surface. At the opening end of the cavity, the rim of the cylindrical coupler forms an O-ring 135 to enhance the tightness of the grip of the engagement between coupling cylinder 130 and connector surface. The O-ring 135 also serves the purpose of forming a seal to create an enclosed space between connector and the coupling cylinder 130. O-ring structure 135 at the open distal end 134 of the coupling cylinder 130 is able to seal any liquid reagent exiting from the reagent compartment upon mounting the device 100 onto connectors to prevent reagent leakage. In one or more embodiments, the O-ring 135 is made of an elastomeric material that is flexible and retains its original shape in an initial state. Upon insertion of a connector with the coupling cylinder 130, the O-ring 135 expands to accommodate the connector creating a tight seal around the connector. Upon removal of the connector, the O-ring 135 returns to its initial state.

In one or more embodiments, the open distal end 124 of the cap body 120 is situated on approximately a same horizontal plane P as the distal tip 158 of the reagent compartment 150 in an initial state such that when a female luer connector or a male luer connector is engaged to the device 100, the reagent compartment 150 is compressed and the reagent compartment 150 retracts towards the proximal wall 126. Distal tip 158 serves as a fluid path blocker to block the ingress of antimicrobial reagent when pressed against an entry port of a male luer connector upon mounting of the device 100 onto a male connector. The distal tip 158 of the reagent compartment 150 is conically shaped and is composed solidly of an elastomeric material for blocking the fluid path as shown in FIGS. 17-19. The distal tip 158 offers a mechanism to block the fluid path in closed female connector and male connector to prevent ingress of the disinfectant or antimicrobial agent into lumens of the respective female connector or male connectors. In one or more embodiments, reagent compartment 150 can be inserted into the inner lumen of stopcocks. The outer diameter of the distal tip 158 of the reagent compartment 50 is compatible with that of open female luer connectors. Distal tip 158 can be compressed by male luer connectors and closed female luer connectors. Upon compression, enclosed disinfectant or antimicrobial agent retreats into the bulb compartment 160.

Distal tip 158 is pressed against entry port of male or female luer connectors upon mounting of the device 100 onto male or female connectors, to block the ingress of disinfectant or antimicrobial agent.

In one or more embodiments, the bulb compartment 160 and the reagent compartment 150 are attached via the aperture 127 located in the proximal wall 126 of proximal end 125 of the cap body 120. The cap body 120 also functions as a mechanical barrier to prevent inadvertent compression of reagent compartment 150. The cap body 120 is composed of rigid materials including polypropylene, high-density polyethylene (HDPE), polypropylene (PP)/thermoplastic elastomer (TPE) blend, or polyethylene (PE)/thermoplastic elastomer (TPE) blend, or polypropylene (PP)/polyethylene (PE) material with a layer of thermoplastic elastomer (TPE) coat. In one or more embodiments, the cap body may be made using a 2-shot molding process.

In one or more embodiments, the coupling cylinder 130, the reagent compartment 150 and the bulb compartment 160 are can be mechanically connected and can be formed as a single entity, as shown in FIG. 13. In one or more embodiment, the boundary of bulb compartment 160 and the reagent compartment 150 may be joined by ultrasonic welding or an adhesive. In an alternate embodiment, the coupling cylinder 130, the reagent compartment 150 and the bulb compartment 160 constitute three structurally distinct components.

In one or more embodiments, the device may further include a removable or peelable seal on the open distal end 124 of the cap body 120 to preserve the sterility of the distal tip 158, inner cavity and open distal end. In one or more embodiments, the removable or peelable seal may include an aluminum or multi-layer polymer film peel back top.

Figure 20C:
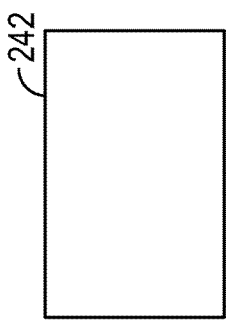
FIG. 20a-20e illustrates a perspective view of a device according to a fourth embodiment in which the coupler is a thin metal sheet.
Figure 20D:
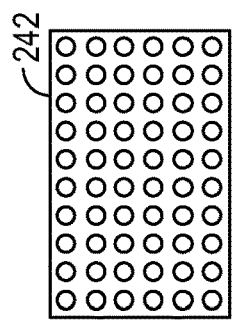
Figure 20E:
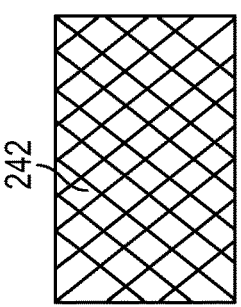
Figure 20B:
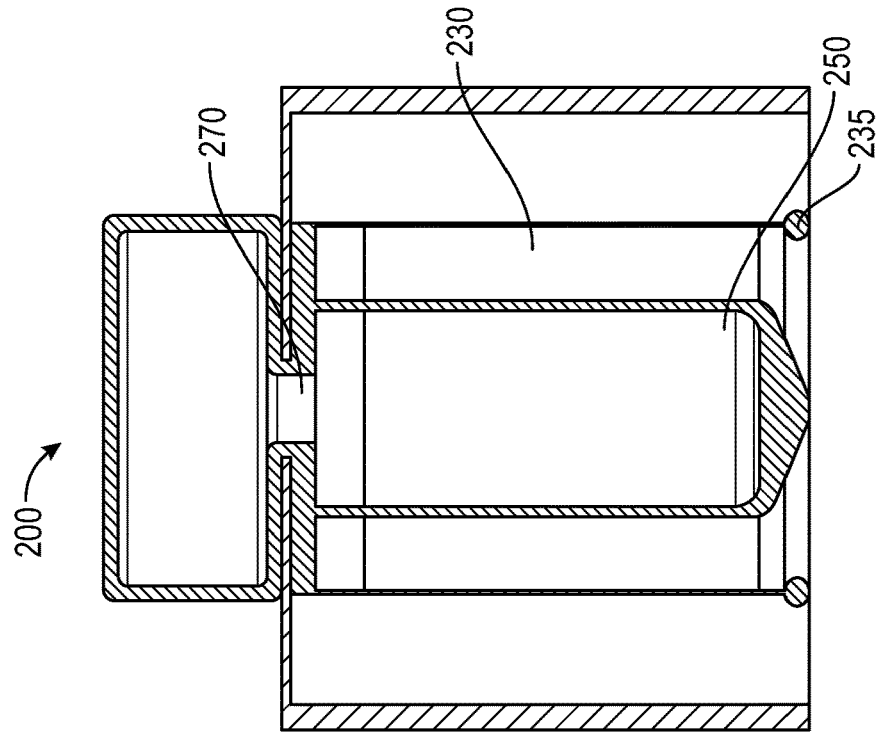
Figure 20A:
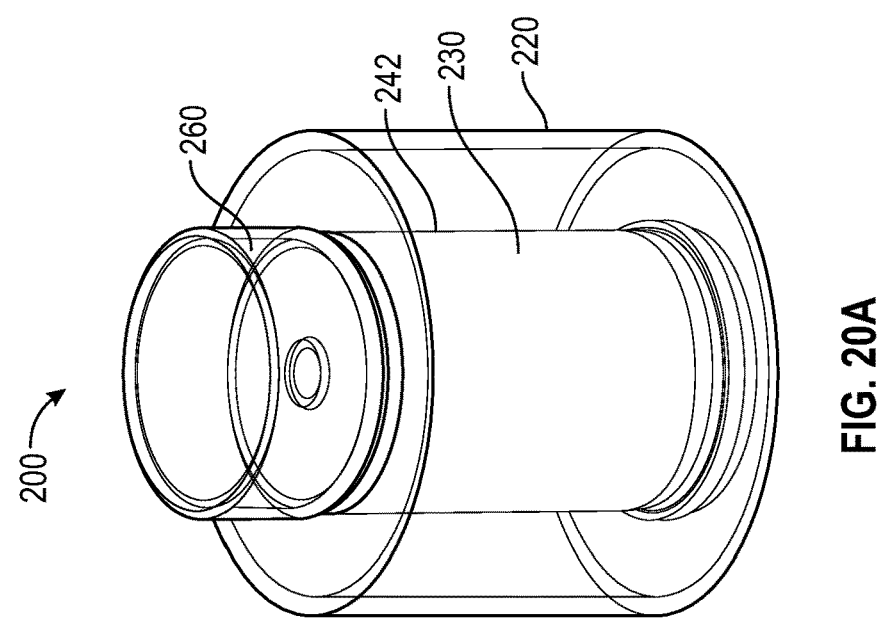

As shown in FIGS. 20a-20e, an alternative embodiment of present disclosure pertains to an alternate mechanism of strengthening the sidewall of the coupling cylinder. As shown in FIGS. 20a-20b, device 200 includes a cap body 220, a coupling cylinder 230, a bulb compartment 260, a reagent compartment 250 and a passageway 270 connecting the bulb compartment 260 to the reagent compartment 250. Side wall 221 having an outside surface 222 and an inside surface 223, an open distal end 224, and a proximal end 225. The proximal end 225 of the cap body 220 includes a proximal wall 226 having an aperture 227. In one or more embodiments, the passageway is positioned in the aperture of the proximal wall. In one or more embodiments, the bulb compartment 260 and the reagent compartment 250 are attached via the aperture 227 located in the proximal wall 226 of proximal end 225 of the cap body 220. The cap body 220 also functions as a mechanical barrier to prevent inadvertent compression of reagent compartment 250. The cap body 220 is composed of rigid materials including polypropylene, high-density polyethylene (HDPE), polypropylene (PP)/thermoplastic elastomer (TPE) blend, or polyethylene (PE)/thermoplastic elastomer (TPE) blend, or polypropylene (PP)/polyethylene (PE) material with a layer of thermoplastic elastomer (TPE) coat. In one or more embodiments, the cap body may be made using a 2-shot molding process.

The coupling cylinder may be made of a semi-rigid material such as thermoplastic elastomer (TPE), a polypropylene (PP)/thermoplastic elastomer (TPE) blend, or polyethylene (PE)/thermoplastic elastomer (TPE) blend, or polypropylene (PP)/polyethylene (PE) material with a layer of thermoplastic elastomer (TPE) coat or other mixture of plastic and thermoplastic elastomer, thermoplastic elastomer (TPE) or rubber of similar elasticity. In one or more embodiments, the coupling cylinder may be made using a 2-shot molding process.

The coupling cylinder 230 is used to engage the threaded surface of luer connectors, including the threaded surface of needle-free connectors, threaded surface of the open female luer of stopcocks, and the threaded surface of the collar of male connectors. As shown in FIG. 20a and FIG. 20b, the coupling cylinder 230 is composed of either a cylindrical thin wall constituted by a metal sheet 242, as shown in FIG. 20c, or a metal sheet 242 that is perforated, as shown in FIG. 20d, or a metal sheet 242 that is meshed, as shown in FIG. 20e, to provide a strengthening component to the sidewall of the coupling cylinder 230. Such a thin wall strengthening structure affords mechanical strength to the coupling cylinder 230 for maintaining geometrical integrity of the coupling cylinder 230, meanwhile it does not completely compromises the flexibility of the coupling cylinder 230 so the coupling cylinder 230 is still bendable to conform to the shape of connectors upon which the device 200 is mounted.

Reagent compartment 250 defines a chamber containing a disinfectant or antimicrobial agent. The reagent compartment 250 includes a sidewall 251 having an exterior wall surface 252, an interior wall surface 254, an array of resealable pores 256 densely integrated into the exterior wall surface 252 and the interior wall surface 254 of the reagent compartment 250, and a distal tip 258. In one or more embodiments, a permeable membrane 255 is disposed between the exterior wall surface 252 and the interior wall surface 254 of the reagent compartment 250. A permeable membrane 255 is either attached to the compartment boundary as a separate layer or embedded into the boundary material to serve as a barrier to prevent enclosed liquid from leaking. In one or more embodiments, the permeable membrane has smaller pores than the pores of the reagent compartment material.

A passageway 228 connects the bulb compartment 260 to the reagent compartment 250. In one or more embodiments, the passageway 228 is positioned in the aperture 227 of the proximal wall 226.

Sidewall 251 of the reagent compartment 250 is perforated by densely distributed micro-sized or nano-sized pores 256 densely integrated into the exterior wall surface 252 and the interior wall surface 254 of the reagent compartment 250.

In one or more embodiments, the reagent compartment 250 is activatable by compressing the upper bulb compartment 260 that protrudes above the cap body 220. When the bulb compartment 260 is squeezed, the increase pressure due to compressed air applies force to reagents in the reagent compartment 250, resulting in the release of the reagent through sidewall 251 of the reagent compartment 250.

Reagent compartment 250 can be inserted into the inner lumen of stopcocks. Its outer diameter is compatible with that of open female luers. It can be compressed by male luer and closed female luer. Upon compression, enclosed fluid retreats into the bulb compartment 260.

The reagent compartment 250 is designed to be compatible in interacting with various disinfectant or antimicrobial agent. In one or more embodiments, the disinfectant or antimicrobial reagent may include variations of alcohol or chlorhexidine. The disinfectant or antimicrobial reagents can be a fluid or a gel selected from the group consisting essentially of isopropyl alcohol, ethanol, 2-propanol, butanol, methylparaben, ethylparaben, propylparaben, propyl gallate, isopropanol, butylated hydroxyanisole (BHA), butylated hydroxytoluene, t-butyl-hydroquinone, chloroxylenol, chlorohexidine, chlorhexidine acetate, chlorhexidine diacetate, chlorhexidine gluconate, povidone iodine, alcohol, dichlorobenzyl alcohol, dehydroacetic acid, hexetidine, triclosan, hydrogen peroxide, colloidal silver, benzethonium chloride, benzalkonium chloride, octenidine, octenidine dihydrochloride, antibiotic, and mixtures thereof. The reagent fills the reagent-containing compartment 250 which constitutes the lower compartment partially surrounded by a coupling cylinder 230, while leaving upper portion of the antimicrobial reagent-containing compartment 250 filled with air. In one or more embodiments, the antimicrobial reagent-containing compartment 250 is composed of a stretchable material such as elastomer, e.g. thermoplastic elastomer.

Coupling cylinder 230 is a cylindrical structure with opening at the bottom. The inner surface matches the outer threaded surface of open or closed female connectors, and hemodialysis connectors. The outer surface matches the threaded surface of the collar on male connectors.

O-ring structure 235 at the open distal end 234 of the coupling cylinder 230 is able to seal the liquid disinfectant or antimicrobial agent upon mounting the device 200 onto connectors to prevent leakage of the disinfectant or antimicrobial agent. In one or more embodiments, O-ring 235 is integrated at the open distal end of the coupling cylinder 230 for a tight grip on connector surface. At the opening end of the cavity, the rim of the cylindrical coupler forms an O-ring 235 to enhance the tightness of the grip of the engagement between coupling cylinder 230 and connector surface. The O-ring 235 also serves the purpose of forming a seal to create an enclosed space between connector and the coupling cylinder 230. O-ring structure 235 at the open distal end 234 of the coupling cylinder 230 is able to seal any liquid reagent exiting from the reagent compartment upon mounting the device 200 onto connectors to prevent reagent leakage. In one or more embodiments, the O-ring 235 is made of an elastomeric material that is flexible and retains its original shape in an initial state. Upon insertion of a connector with the coupling cylinder 230, the O-ring 235 expands to accommodate the connector creating a tight seal around the connector. Upon removal of the connector, the O-ring 235 returns to its initial state.

In one or more embodiments, the open distal end 224 of the cap body 220 is situated on approximately a same horizontal plane P as the distal tip 258 of the reagent compartment 250 in an initial state such that when a female luer connector or a male luer connector is engaged to the device 200, the reagent compartment 250 is compressed and the reagent compartment 250 retracts towards the proximal wall 226. Distal tip 258 serves as a fluid path blocker to block the ingress of antimicrobial reagent when pressed against an entry port of a male luer connector upon mounting of the device 200 onto a male connector. The distal tip 258 of the reagent compartment 250 is conically shaped and is composed solidly of an elastomeric material for blocking the fluid path. The distal tip 258 offers a mechanism to block the fluid path in closed female connector and male connector to prevent ingress of the disinfectant or antimicrobial agent into lumens of the respective female connector or male connectors. In one or more embodiments, reagent compartment 250 can be inserted into the inner lumen of stopcocks. The outer diameter of the distal tip 258 of the reagent compartment 50 is compatible with that of open female luer connectors. Distal tip 258 can be compressed by male luer connectors and closed female luer connectors. Upon compression, enclosed disinfectant or antimicrobial agent retreats into the bulb compartment 260.

Distal tip 258 is pressed against entry port of male or female luer connectors upon mounting of the device 200 onto male or female connectors, to block the ingress of disinfectant or antimicrobial agent.

In one or more embodiments, the coupling cylinder 230, the reagent compartment 250 and the bulb compartment 260 are can be mechanically connected and can be formed as a single entity, as shown in FIGS. 20a and 20b. In one or more embodiment, the boundary of bulb compartment 260 and the reagent compartment 250 may be joined by ultrasonic welding or an adhesive. In an alternate embodiment, the coupling cylinder 230, the reagent compartment 250 and the bulb compartment 260 constitute three structurally distinct components.

In one or more embodiments, the device may further include a removable or peelable seal on the open distal end 224 of the cap body 220 to preserve the sterility of the distal tip 258, inner cavity and open distal end. In one or more embodiments, the removable or peelable seal may include an aluminum or multi-layer polymer film peel back top.

Embodiments of the device 10, 200 and 200 of the present disclosure leverage the compliance of elastomeric material and the compressibility of the space enclosed by such elastomeric material. The design is based on the usage of elastomeric material to form components that fit the needs for a disinfecting cap that can accommodate different types of luer fitting, and can release antimicrobial material for disinfection in a manner that is compatible with the cleaning needs for different types of luer connectors. Embodiments of the present disclosure also combine compliant material with rigid material to create a composite that is deformable to conform to various geometry yet maintains structural strength to meet the need of both the aspect of fitting onto connectors, and the aspect of sealing the space of disinfecting to fulfill both prevention of antimicrobial reagent leakage, and creation of mechanical barrier to mitigate contamination.

In one or more embodiment, the device 10, 100 and 200 of the present disclosure may be manufactured in accordance with an injection molding or blow-fill-seal technique of a character well understood by those skilled in the art.

The concept of a blow-fill-seal process is that a container is formed, filled, and sealed as a unitary container in a continuous manner without human intervention in a sterile, enclosed area inside a machine. Blow-fill-seal manufacturing forms a closed container by extruding and forming a parison within a mold, filling the container and sealing the container in a single step. This manufacturing process enables the device to be produced in a single process. For example, pharmaceutical grade resin is extruded into a tube, which is then formed into a bulb compartment and reagent compartment. A mandrel is inserted into the newly formed bulb compartment and reagent compartment and filled. The bulb compartment and reagent compartment is then sealed and joined with a cap body, all inside a sterile, shrouded chamber. The device is then discharged to a non-sterile area for packaging and distribution. This blow-fill-seal technique comprises the continuous extrusion through an extruder head of a length of a parison in the form of a hollow tube between and through two co-acting first or main mold halves. The method includes the step of cutting off the parison below the extruder head and above the main mold halves to create an opening which allows a blowing and filling nozzle assembly to be moved downwardly into the opening in the parison for molding and thereafter filling a molded bulb compartment and reagent compartment. When the container portion of the container assembly is filled with the desired amount of liquid disinfectant or antimicrobial agent, the blowing and filling nozzle assembly is retracted from the opening in the parison. A separate pair of co-acting second or upper sealing mold halves are then moved together around the exposed length of parison to form and seal the bulb compartment upper portion. The finished assembly, completely formed, filled, and sealed as a unitary structure is then conveyed out of the molding apparatus.

Embodiments of the present disclosure may be used with access ports, including needle-free connectors, male luer connectors on IV lines/extensions, open female luer on stopcocks, and hemodialysis connectors for disinfecting purpose. In some embodiments, the connector comprises a needleless injection site, which may sometimes be referred to as a needleless injection port, hub, valve, or device, or as a needleless access site, port, hub, valve, or device. In one or more embodiments, the female connector may be a needle-free connector, stopcock, or hemodialysis connector. In one or more embodiments, the needleless connector is selected from a Q-Syte connector, MaxPlus, MaxPlus Clear, MaxZero, UltraSite, Caresite, InVision-Plus, Safeline, One-Link, V-Link, ClearLink, NeutraClear, Clave, MicroClave, MicroClave Clear, Neutron, NanoClave, Kendall, Nexus, InVision, Vadsite, Bionector, etc. In one or more embodiments, the male connector may be an intravenous tubing end or stopcock.

In some embodiments, the device 10, 100 and 200 of the present disclosure can be connected with any of a variety of different needleless injection sites, such as those previously listed. Use of the device 10, 100 and 200 of the present disclosure replaces the standard swabbing protocol for cleaning connectors.

Reference throughout this specification to "one embodiment," "certain embodiments," "one or more embodiments" or "an embodiment" means that a particular feature, structure, material, or characteristic described in connection with the embodiment is included in at least one embodiment of the disclosure. Thus, the appearances of the phrases such as "in one or more embodiments," "in certain embodiments," "in one embodiment" or "in an embodiment" in various places throughout this specification are not necessarily referring to the same embodiment of the disclosure. Furthermore, the particular features, structures, materials, or characteristics may be combined in any suitable manner in one or more embodiments.

Although the disclosure herein has provided a description with reference to particular embodiments, it is to be understood that these embodiments are merely illustrative of the principles and applications of the present disclosure. It will be apparent to those skilled in the art that various modifications and variations can be made to the method and apparatus of the present disclosure without departing from the spirit and scope of the disclosure. Thus, it is intended that the present disclosure include modifications and variations that are within the scope of the appended claims and their equivalents.

What is claimed is:

1. A device for connection to a medical connector, the device comprising:
   a cap body comprising a side wall having an outside surface and an inside surface, an open distal end, and a proximal end including a proximal wall, the proximal wall having an aperture, the side wall having a length extending from the proximal end to the open distal end, the open distal end defining an end face;
   a coupling cylinder concentrically placed within the cap body and having a side wall with an inner surface that mates to an outer threaded surface of a female connector or a hemodialysis connector, an outer surface that mates to a threaded surface of a collar on a male connector, a distal end and a proximal end;
   a bulb compartment protruding above the cap body and filled with air;
   a reagent compartment surrounded by the coupling cylinder and connected to the bulb compartment, the reagent compartment having a boundary sidewall defining a chamber containing a disinfectant or antimicrobial agent, the boundary sidewall of the reagent compartment having an exterior wall surface, an interior wall surface, an array of resealable pores densely integrated and embedded in a polymer matrix of the exterior wall surface and the interior wall surface of the reagent compartment, and a distal tip; and
   a passageway connecting the bulb compartment to the reagent compartment, the passageway positioned in the aperture of the proximal wall.

2. The device of claim 1, wherein the distal end of the coupling cylinder includes an O-ring.

3. The device of claim 2, wherein the O-ring is made of an elastomeric material.

4. The device of claim 1, wherein the side wall of the coupling cylinder includes one or more leaf springs.

5. The device of claim 1, wherein the open distal end of the cap body is situated on approximately a same horizontal plane P as the distal tip of the reagent compartment in an initial state.

6. The device of claim 1, wherein when a female luer connector or a male luer connector is engaged to the device, the reagent compartment is compressed and retracts towards the proximal wall.

7. The device of claim 6, wherein the compression of the reagent compartment releases the disinfectant or antimicrobial agent from the reagent compartment to disinfect the female luer connector or the male luer connector.

8. The device of claim 1, wherein the disinfectant or antimicrobial agent is selected from the group consisting of isopropyl alcohol, ethanol, 2-propanol, butanol, methylparaben, ethylparaben, propylparaben, propyl gallate, butylated hydroxyanisole (BHA), butylated hydroxytoluene, t-butyl-hydroquinone, chloroxylenol, chlorohexidine, chlorhexidine diacetate, chlorohexidine gluconate, povidone iodine, alcohol, dichlorobenzyl alcohol, dehydroacetic acid, hexetidine, triclosan, hydrogen peroxide, colloidal silver, benzethonium chloride, benzalkonium chloride, octenidine, antibiotic, and mixtures thereof.

9. The device of claim 1, wherein the disinfectant or antimicrobial agent is a fluid or a gel.

10. The device of claim 1, wherein the female connector is selected from a group consisting of needle-free connectors, stopcocks, and hemodialysis connectors.

11. The device of claim 1, wherein the male connector is an intravenous tubing end or stopcock.

12. The device of claim 1, further comprising a peelable seal on the open distal end of the cap body.

13. The device of claim 12, wherein the peelable seal comprises an aluminum or multi-layer polymer film peel back top.

14. The device of claim 1, further comprising a permeable membrane disposed between the exterior wall surface and the interior wall surface of the reagent compartment.

15. The device of claim 1, wherein the coupling cylinder side wall is made of a thin sheet of metal.

16. The device of claim 15, wherein the thin sheet of metal is perforated.

17. The device of claim 15, wherein the thin sheet of metal is meshed.

* * * * *